(12) United States Patent
Rock et al.

(10) Patent No.: US 8,729,065 B2
(45) Date of Patent: *May 20, 2014

(54) CRYSTALLINE FORMS OF A PHARMACEUTICAL COMPOUND

(75) Inventors: Michael Harold Rock, Hvidovre (DK); Heidi Lopez De Diego, Naerum (DK); Kim Lasse Christensen, Slagelse (DK); Ole Nielsen, Valby (DK); Anders Buur, Allerod (DK); Mark Howells, Havdrup (DK)

(73) Assignee: Cephalon, Inc., Frazer, PA (US)

( * ) Notice: Subject to any disclaimer, the term of this patent is extended or adjusted under 35 U.S.C. 154(b) by 118 days.

This patent is subject to a terminal disclaimer.

(21) Appl. No.: 12/983,558

(22) Filed: Jan. 3, 2011

(65) Prior Publication Data

US 2011/0124629 A1 May 26, 2011

Related U.S. Application Data

(63) Continuation of application No. 10/597,977, filed as application No. PCT/DK2005/000127 on Feb. 24, 2005, now Pat. No. 8,076,320.

(60) Provisional application No. 60/548,351, filed on Feb. 27, 2004.

(30) Foreign Application Priority Data

Feb. 27, 2004 (DK) .................................. 2004 00326

(51) Int. Cl.
*A61P 25/16* (2006.01)
*A61K 31/553* (2006.01)
*C07D 498/12* (2006.01)

(52) U.S. Cl.
USPC ..................................... 514/211.08; 540/545

(58) Field of Classification Search
USPC ..................................... 514/211.08; 540/545
See application file for complete search history.

(56) References Cited

U.S. PATENT DOCUMENTS 5,621,100 A 4/1997 Lewis et al.

FOREIGN PATENT DOCUMENTS

| EP | 0 651 754 B1 | 4/1997 |
| EP | 1 121 932 A1 | 8/2001 |
| WO | 94/02488 | 2/1994 |
| WO | 97/49406 | 12/1997 |

OTHER PUBLICATIONS

Kaneko et al., "Neurotrophic 3,9-Bis[(alkylthio)methyl]- and -Bis(alkoxymethyl)-K-252a Derivatives", J. Med. Chem. (1997), vol. 40, pp. 1863-1869.
Pirvola et al., "Rescue of Hearing, Auditory Hair Cells, and Neurons by CEP-1347/KT7515, an Inhibitor of c-Jun N-Terminal Kinase Activation", Neuroscience (2000), vol. 20(1), pp. 43-50.
Murakata et al., "Mixed Lineage Kinase Activity of Indolocarbazole Analogues", Bioorg. Med. Chem. Lett. (2002), vol. 12, pp. 147-150.
Saporito et al., "Preservation of Cholinergic Activity and Prevention of Neuron Death by CEP-1347/KT-7515 Following Excitotoxic Injury of the Nucleus Basalis Magnocellularis", Neuroscience (1998), vol. 86(2), pp. 461-472.
Ylikoski et al., "Blockade of c-Jun N-terminal kinase pathway attenuates gentamicin-induced cochlear and vestibular hair cell death", Hearing Research (2002), vol. 166, pp. 33-43.
Maroney et al., "Mixed Lineage Kinase Family, Potential Targets for Preventing Neurodegeneration", Curr. Med. Chem.—Central Nervous System Agents (2002), vol. 2, pp. 143-155.
Bozyczko-Coyne et al., "CEP-1347/KT-7515, an inhibitor of SAPK/JNK pathway activation, promotes survival and blocks multiple events associated with AB-induced cortical neuron apoptosis", J. Neurochemistry (2001), vol. 77, pp. 849-863.
Bodner et al., "Mixed lineage kinase 3 mediates gp 120IIIB-induced neurotoxicity", J. Neurochemistry (2002), vol. 82, pp. 1424-1434.
Mucke, "CEP-1347 Cephalon", IDRUGS (2003), vol. 6(4), pp. 377-383.
Saporito et al., "Discovery of CEP-1347/KT-7515, an Inhibitor of the JNK/SAPK Pathway for the Treatment of Neurodegenerative Diseases", Progress in Medicinal Chemistry (2002), vol. 40, pp. 23-62.

*Primary Examiner* — Brenda Coleman

(57) ABSTRACT

Described are crystalline forms of the pharmaceutical compound "[9S-(9α,10β,12α)]-5,16-Bis[(ethylthio)methyl]-2,3,9,10,11,12-hexahydro-10-hydroxy-9-methyl-1-oxo-9,12-epoxy-1H-diindolo[1,2,3-fg:3',2',1'-kl]pyrrolo[3,4-i][1,6]benzodiazocine-10-carboxylic acid methyl ester", as well as methods for their use and preparation.

18 Claims, 19 Drawing Sheets

Alpha form

Gamma form

Alpha form

Beta form

CRYSTALLINE FORMS OF A PHARMACEUTICAL COMPOUND

CROSS REFERENCE TO RELATED APPLICATIONS

This is a continuing application of U.S. application Ser. No. 10/597,977 filed Sep. 12, 2006, which is a U.S. national phase application under 35 U.S.C. §371 of International Patent Application No. PCT/DK2005/000127 filed Feb. 24, 2005, which claims priority of Danish Patent Application No. PA200400326, filed on Feb. 27, 2004, and U.S. Provisional Patent Application No. 60/548,351, filed on Feb. 27, 2004, all of which are hereby incorporated by reference.

FIELD OF THE INVENTION

The present invention relates to crystalline forms of a compound and the use of such forms in the preparation of a medicament, in particular for the treatment of Parkinson's disease.

BACKGROUND OF THE INVENTION

The compound with the structure outlined below is presently in clinical trials for Parkinson's disease (Idrugs, 2003, 6(4), 377-383).

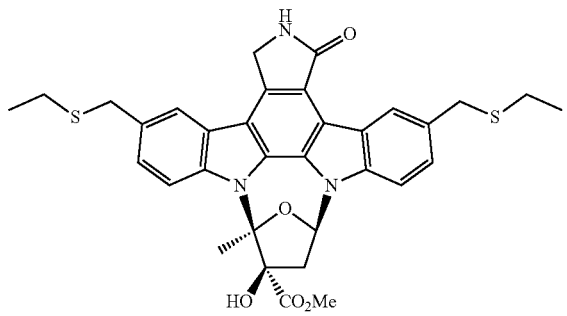 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

This compound is in the following referred to as Compound I. The chemical name of Compound I is [9S-(9α,10β, 12α)]-5,16-Bis[(ethylthio)methyl]-2,3,9,10,11,12-hexahydro-10-hydroxy-9-methyl-1-oxo-9,12-epoxy-1H-diindolo[1,2,3-fg:3',2',1'-kl]pyrrolo[3,4-i][1,6]benzodiazocine-10-carboxylic acid methyl ester.

The following references relate to Compound I, in particular to methods for its preparation [J. Med. Chem. 1997, 40(12), 1863-1869; Curr. Med. Chem.—Central Nervous System Agents, 2002, 2(2), 143-155] and its potential medical uses, mainly in diseases in the central nervous system (CNS), in particular for treatment of neurodegenerative diseases, e.g. Parkinson's disease, Alzheimer's disease, Huntington's disease, peripheral neuropathy, AIDS dementia, and ear injuries such as noise-induced hearing loss [Progress in Medicinal Chemistry (2002), 40, 23-62; Bioorg. Med. Chem. Lett. 2002, 12(2), 147-150; Neuroscience, Oxford, 1998, 86(2), 461-472; J. Neurochemistry (2001), 77(3), 849-863; J. Neuroscience (2000), 20(1), 43-50; J. Neurochemistry (2002), 82(6), 1424-1434; Hearing Research, 2002, 166(1-2), 33-43].

The following patent documents relate to Compound I, including its medical use and synthesis: WO 9402488, WO9749406, U.S. Pat. No. 5,621,100, EP 0651754 and EP 112 932.

By the known methods, Compound I is synthesized in a solid amorphous form. The inventors have now discovered 5 crystalline forms of Compound I (named alpha, beta, gamma, delta and epsilon) thereby providing an opportunity to improve the manufacturing process of Compound I and its pharmaceutical use. There exists a need for crystalline forms, which may exhibit desirable and beneficial chemical and physical properties. There also exists a need for reliable and reproducible methods for the manufacture, purification, and formulation of Compound I to permit its feasible commercialisation.

SUMMARY OF THE INVENTION

In a first aspect the present invention relates to crystalline Compound I, in particular to crystalline forms of Compound I.

Accordingly, the invention provides a crystalline form of Compound I named alpha and characterized by one or more of: (i) the X-Ray powder diffractogram shown in FIG. 1 as measured using CuKα radiation; (ii) an X-Ray powder diffractogram as measured using CuKα radiation having reflections at 2θ angles: 5.2, 7.3, 8.1, 10.1, 10.4, 11.2, 13.2, 15.1, 15.5, 17.3, 21.7, 23.8, 25.1 (iii) the solid state Carbon-13 NMR spectrum shown in FIG. 7; (iv) the NIR reflectance spectrum shown in FIG. 10.

In a further aspect the invention provides a crystalline form of Compound I named beta and characterized by one or more of: (i) the X-Ray powder diffractogram shown in FIG. 2 as measured using CuKα radiation; (ii) an X-Ray powder diffractogram as measured using CuKα radiation having reflections at 2θ angles: 6.6, 8.9, 10.7, 11.4, 11.7, 13.7, 17.0, 18.5, 18.8, 19.2, 20.3, 24.4, 30.6; (iii) the solid state Carbon-13 NMR spectrum shown in FIG. 8; (iv) the NIR reflectance spectrum shown in FIG. 11.

In a still further aspect the invention provides a crystalline form of Compound I named gamma and characterized by one or more of: (i) the X-Ray powder diffractogram shown in FIG. 3 as measured using CuKα radiation; (ii) an X-Ray powder diffractogram as measured using CuKα radiation having reflections at 2θ angles: 7.5, 8.3, 9.6, 11.5, 11.8, 12.5, 15.9, 16.3, 16.7, 17.2, 18.0, 19.3, 21.0, 28.1; (iii) the solid state Carbon-13 NMR spectrum shown in FIG. 9; (iv) the NIR reflectance spectrum shown in FIG. 12.

In a further aspect the invention provides a crystalline form of Compound I named delta and characterized by one or more of: (i) the X-Ray powder diffractogram shown in FIG. 13 as measured using CuKα radiation; (ii) an X-Ray powder diffractogram as measured using CuKα radiation having reflections at 2θ angles: 7.3, 8.3, 9.7, 11.1, 11.7, 12.1, 15.6, 16.1, 17.3, 18.3, 20.9, 22.1, 22.2, 25.7, 25.8.

In a further aspect the invention provides a crystalline form of Compound I named epsilon and characterized by one or more of: (i) the X-Ray powder diffractogram shown in FIG. 15 as measured using CuKα radiation; (ii) an X-Ray powder diffractogram as measured using CuKα radiation having reflections at 2θ angles: 8.9, 9.2, 10.2, 12.6, 14.2, 14.6, 17.0, 18.6, 20.4, 21.1, 23.9, 25.2.

The invention further relates to methods for preparing the crystalline forms of the invention and the use of such forms in the preparation of a medicament comprising Compound I as an active ingredient.

Figure 1:
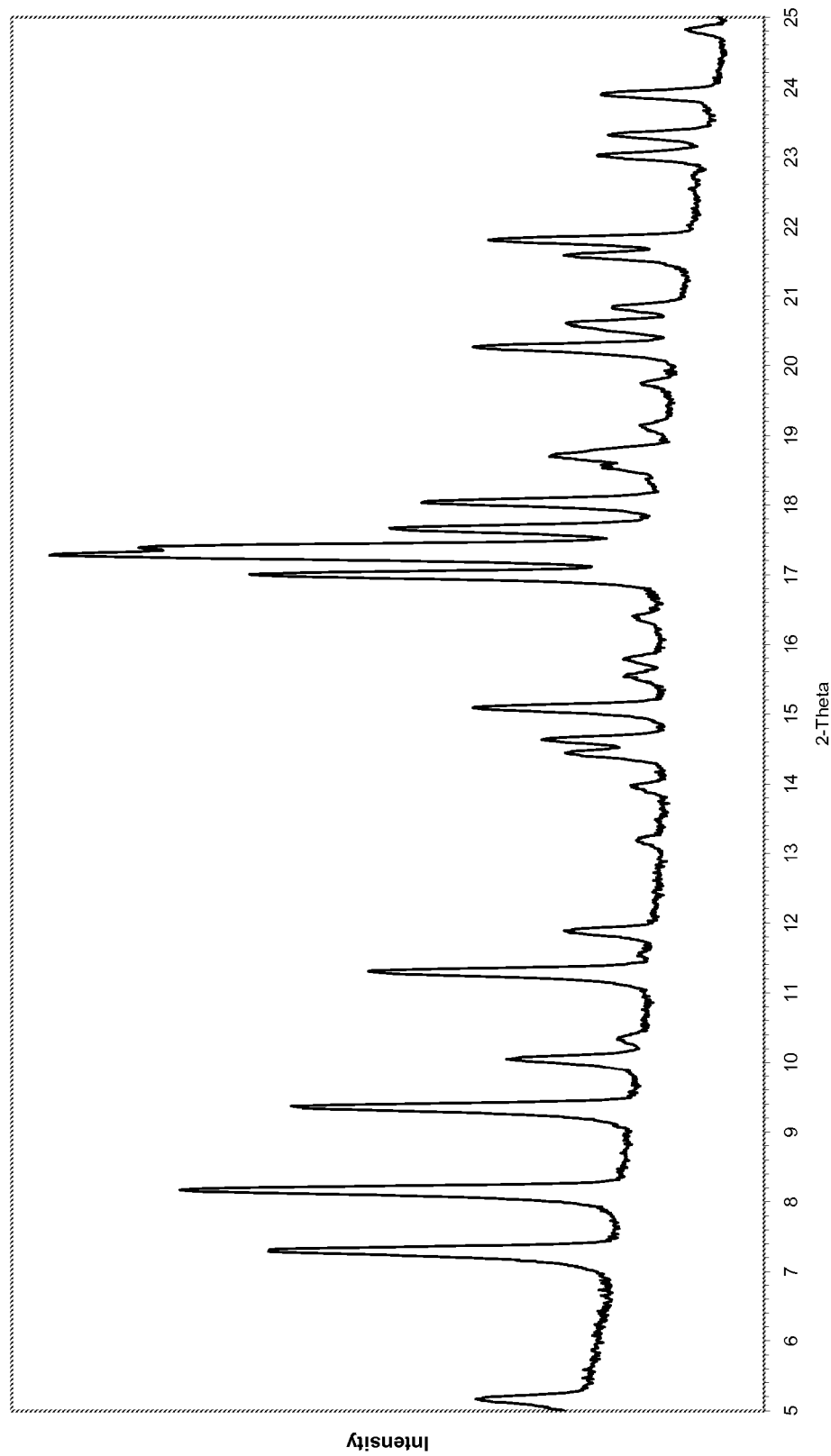
FIG. 1: Shows an x-ray powder diffractogram of Compound I alpha form.

Further details for the figures are revealed in the Examples below.

DETAILED DESCRIPTION OF THE INVENTION

The discovery of a crystalline form of a pharmaceutically useful compound provides an opportunity to improve the performance characteristics of the pharmaceutical product and the manufacturing process.

Differences in physical properties, such as stability (shelf-life), bioavailability, solubility, and dissolution rate, exhibited by the different solid forms of a compound are important factors in the manufacturing and formulation of a compound. Differences in stability can result from changes in chemical reactivity (e.g. oxidation) or mechanical changes (e.g. tablets crumble on storage can lead to the conversion to a thermodynamically more stable crystal form) or both. The physical properties of a solid form are important in processing, e.g. one solid form might be more difficult to filter and wash free of impurities. This can be due to differences in particle shape and size distribution between one crystalline form relative to the other and the amorphous form.

Additionally, for drugs that exist in different crystalline forms and which are sold in solid form it is generally important for both medical and commercial reasons to produce and market a known crystalline form. The discovery of crystalline Compound I and the existence of 5 crystalline forms enable the development of a defined crystalline form in place of an amorphous solid. Also, the physical properties of the crystalline Compound I offer advantages for formulation development and tablet preparation, e.g. direct compression is facilitated by having a defined crystal form.

Crystalline compounds are generally more stable than the corresponding amorphous compound, and this is particularly important in the case of the air sensitive and light sensitive Compound I.

Experiments were carried out in a Heraeus Suntest CPS+ for the crystalline forms alpha, beta and gamma where the solid compound was exposed to light for 14 h at 650 W. The light treatment led to almost 60% degradation of the amorphous substance while the crystalline forms showed less than 30% degradation.

Compound I contains two sulphur atoms and is easily oxidised to a complex mixture of sulphones and sulphoxides. This sensitivity to oxidation requires great care during purification of Compound I. The present invention, which makes purification of Compound I by crystallisation possible, reduces the levels of oxidised compounds as compared to the product obtained when the inventors have used other methods of purification such as chromatography. In addition Compound I contains an active ester group which may undergo transesterification reactions and it is also susceptible to hydrolysis.

In the final step in the synthesis of Compound I, the desired thiol ethyl side chains are introduced using ethyl mercaptan as a reactant [J. Med. Chem. 1997, 40(12), 1863-1869; Curr. Med. Chem.—Central Nervous System Agents, 2002, 2(2), 143-155]. Ethyl mercaptan has a characteristic strong odour, which is undesirable in a pharmaceutical product. The isolation of Compound I as an amorphous solid results in inclusion of ethyl mercaptan in the solid product, while the levels of this undesired reactant is reduced through crystallisation.

Additionally, the physical characteristics of the crystalline forms of the invention improve the isolation step for example by decreasing the filtration times compared to the amorphous form of Compound I, which is of great significance for the large scale manufacturing of Compound I. In this respect the delta form was found to have better filtration properties than the alpha form.

A further difference in the physical chemical properties of the crystalline forms compared to the amorphous form is the higher melting points, cf. Table I below in Example 9, which can give advantages in further processing.

As indicated above the inventors have now discovered that Compound I can be made in a crystalline form and that there is at least 5 crystalline forms Compound I, herein named alpha, beta, gamma, delta and epsilon.

Thus, in a broad aspect the invention relates to crystalline Compound I, in particular to a crystalline form of Compound I. As used herein the expression "a crystalline form of Compound I" comprises any crystalline forms of Compound I, i.e. in contrast to the amorphous form. In particular the term "crystalline Compound I" includes the alpha, beta, gamma, delta and/or epsilon crystalline form of Compound I, which forms are as defined herein.

Crystalline forms of a compound are differentiated by the positions of the atomic nuclei in the unit cell of the solidified compound. The differences produce different macroscopic properties like thermal behaviour, vapour permeability and solubility, which as indicated above have practical consequences in pharmacy. The various forms described herein may be distinguishable from one another through the use of various analytical techniques known to one of ordinary skill in the art. Such techniques include, but are not limited to X-ray powder diffraction (XRD), differential scanning calorimetry (DSC), solid-state nuclear magnetic resonance (NMR) spectroscopy, and Near-infrared (NIR) spectroscopy. Crystalline forms of a compound are most readily distinguished by X-ray analysis. Single crystal X-ray crystallography yields data that can be used to determine the positions of the nuclei, which in turn may be visualized with computer or mechanical models, thus providing a three-dimensional image of the compound. While single crystal X-ray studies provide unmatched structural information, they are expensive and quality data can sometimes be difficult to acquire. Powder X-ray diffraction is used more frequently by the pharmaceutical industry to characterize new crystalline forms of drugs than is single crystal X-ray analysis. Powder X-ray diffraction yields a fingerprint that is unique to the crystalline form and is able to distinguish it from the amorphous compound and all other crystalline forms of the compound.

Figure 4:
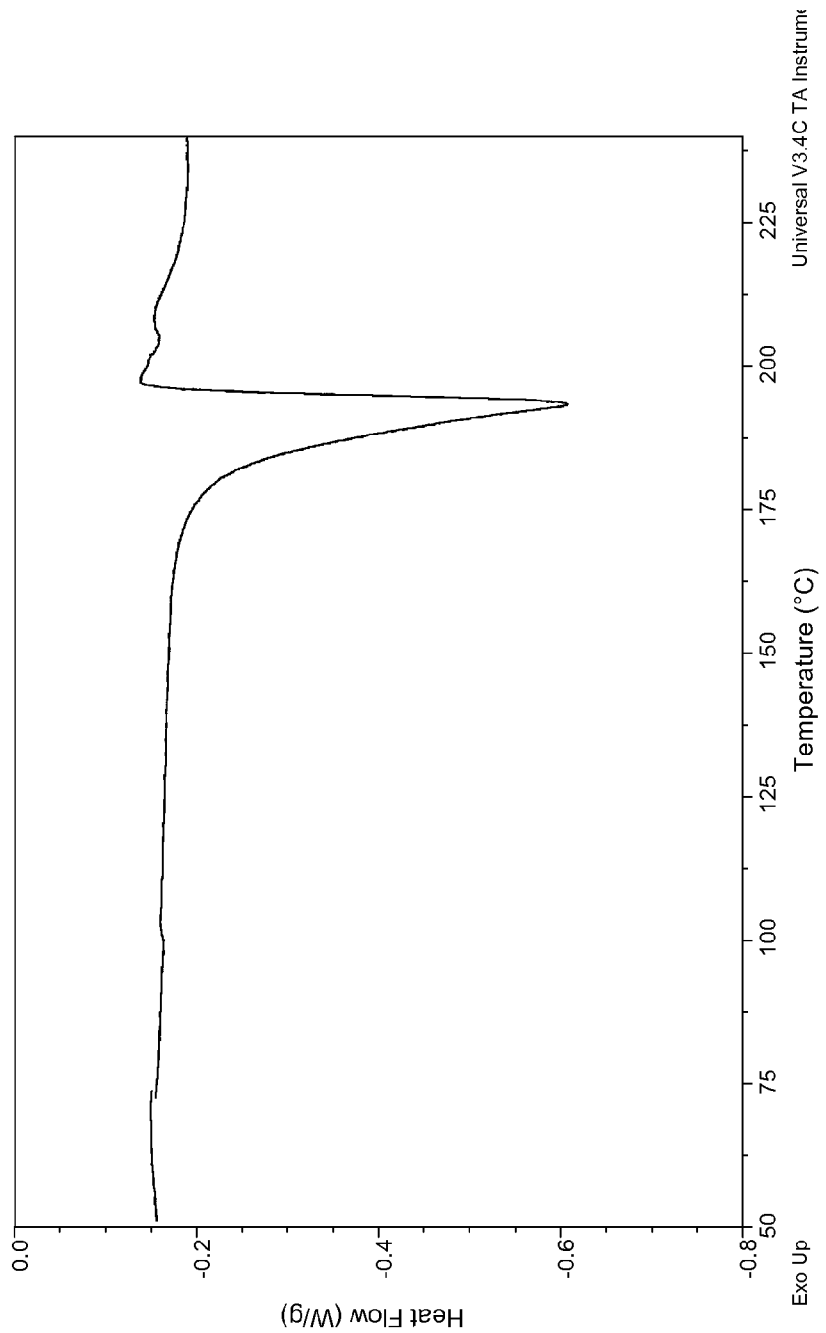
FIG. 4: Shows a DSC thermogram of Compound I alpha form.

Accordingly, one embodiment of the invention relates to a crystalline form of Compound I named alpha characterized by the X-Ray powder diffractogram shown in FIG. 1 as measured using CuKα radiation. In a further embodiment the alpha form of Compound I is characterized by reflections in the X-Ray powder diffractogram as measured using CuKα radiation at 2-theta angles: 5.2, 10.1, 10.4, 13.2, 15.1, 25.1. The alpha form of Compound I may also be characterized by having reflections in the X-Ray diffractogram as measured using CuKα radiation at 2θ angles: 5.2, 7.3, 8.1, 10.1, 10.4, 11.2, 13.2, 15.1, 15.5, 17.3, 21.7, 23.8, 25.1. The alpha form of Compound I may also be characterized by the solid state Carbon-13 NMR spectrum shown in FIG. 7. The alpha form of Compound I may also be characterized by the NIR reflectance spectrum shown in FIG. 10. The alpha form of Compound I may also be characterized by having a melting point in the range of 180-190° C. The alpha form of Compound I may also be characterized by having DSC thermogram substantially in accordance with that shown in FIG. 4. The alpha form of Compound I may also be characterized by a DSC thermogram having an endotherm from about 170° C. to about 200° C. The crystal structure of the alpha form (Example 8.5) has a space in the crystal lattice that may or may not be occupied by a smaller solvent, in particular a water or a methanol molecule. Thus, the crystalline alpha form of Compound I can be a solvate of varying amounts of water and/or methanol.

Accordingly, the invention also relates to a crystal form characterized by having a crystal structure with the following characteristics at 122 K: Space group: P2₁2₁2₁, Unit cell dimensions: a=10.227(2) Å, b=23.942(2) Å and c=24.240(2) Å, α=90°, β=90°, γ=90°, 2 molecules in the asymmetric unit. As the asymmetric unit in this crystal structure contains 2 molecules of Compound I and one solvent site, full occupancy of the solvent site leads to a hemi-solvate. The invention further relates to the above indicated crystal structure having atom positions substantially as described by the coordinates in Tables 2-4.

When indicating herein for the X-Ray powder diffractogram data the reflections (peaks) it is understood that the reflections are expressed in degrees (at 2θ angles, i.e. at 2-theta angles).

Figure 2:
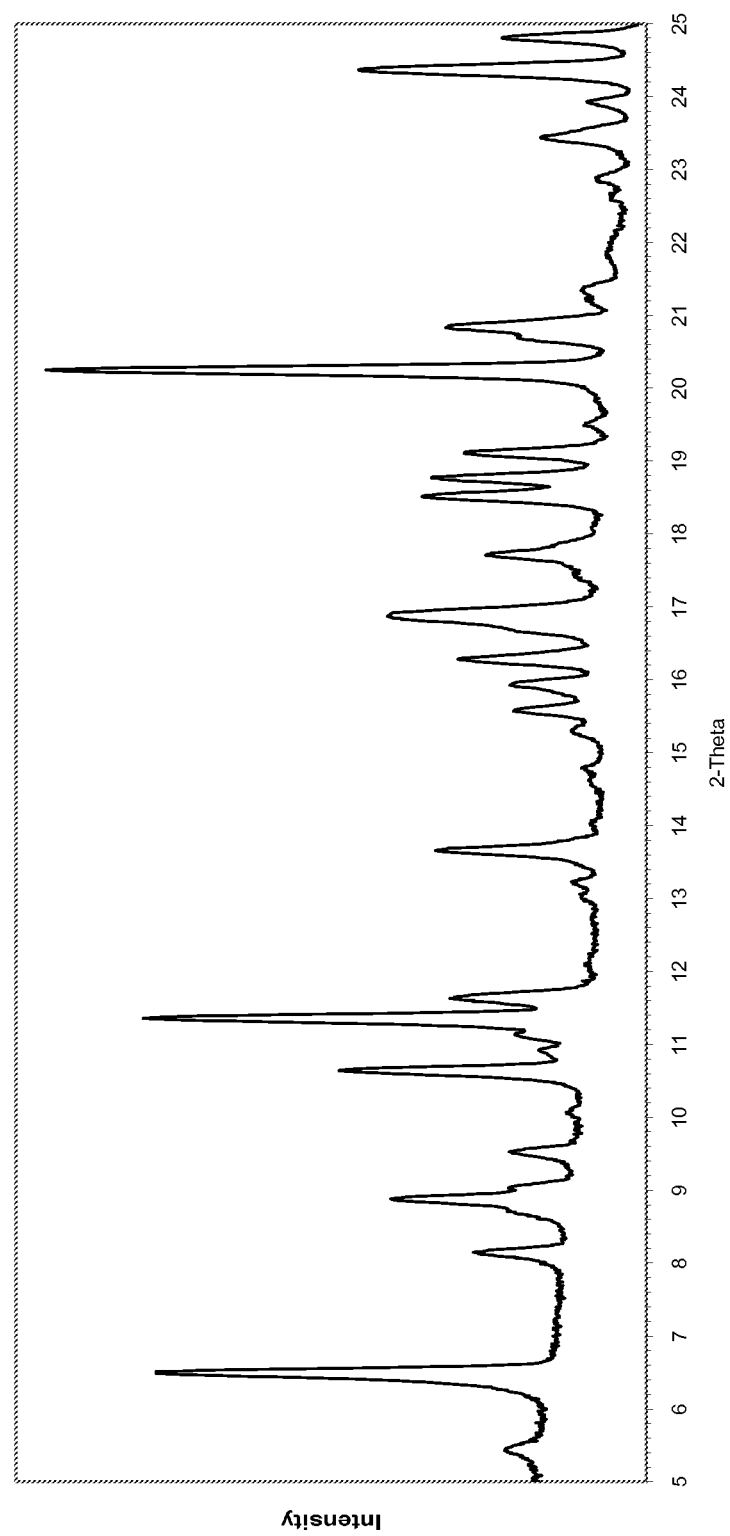
FIG. 2: Shows an x-ray powder diffractogram of Compound I beta form.

A further embodiment relates to a crystalline form of Compound I named beta characterized by the X-Ray powder diffractogram shown in FIG. 2 as measured using CuKα radiation.

Figure 5:
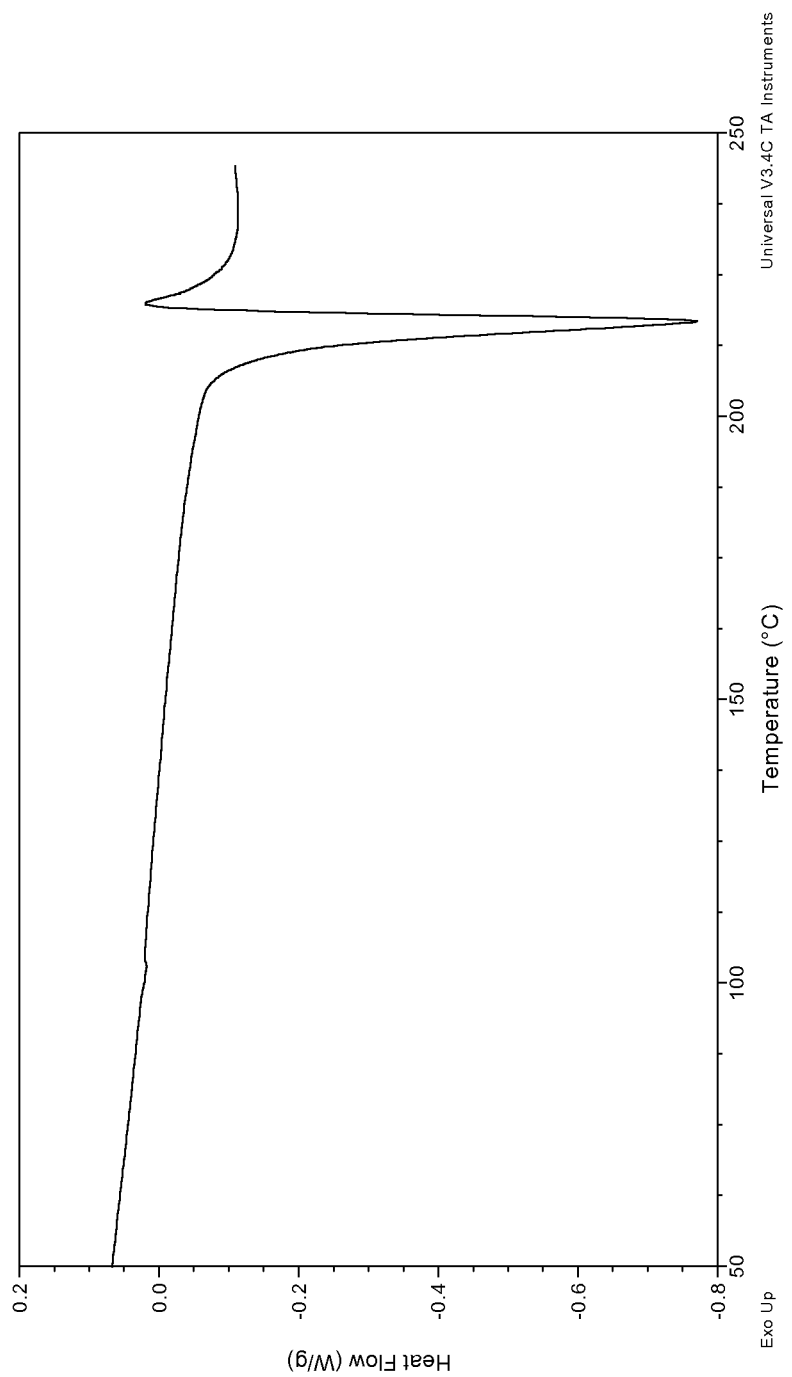
FIG. 5: Shows a DSC thermogram of Compound I beta form.
Figure 8:
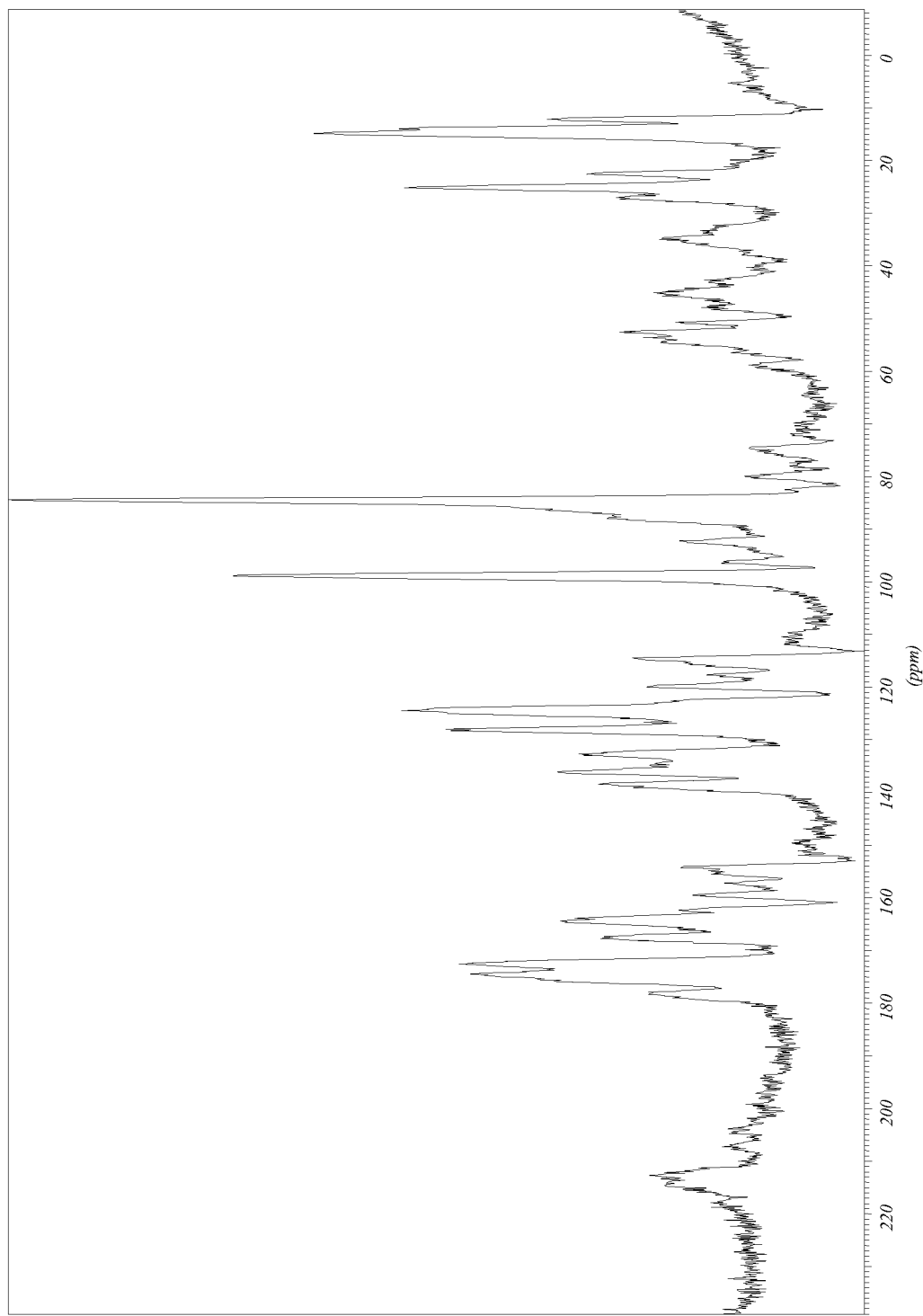
FIG. 8: Shows a solid state Carbon-13 NMR spectrum of Compound I beta form.
Figure 11:
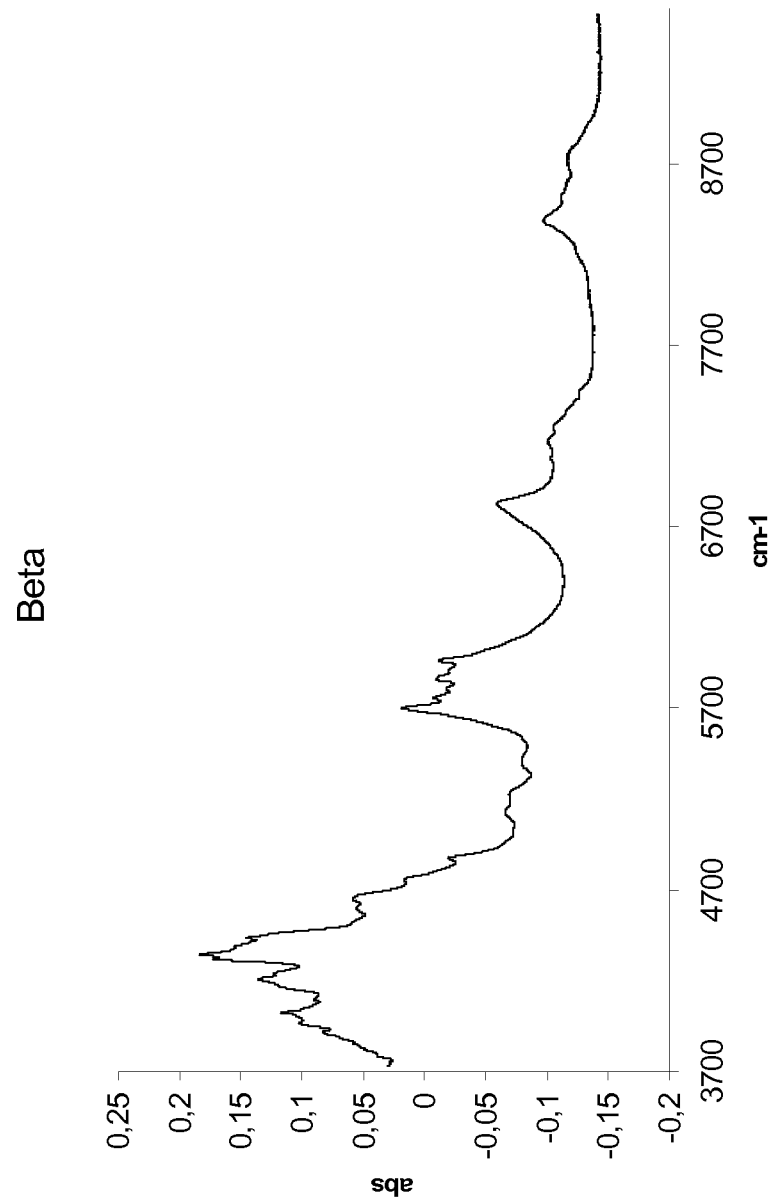
FIG. 11: Shows a NIR reflectance spectrum of Compound I beta form.

In a further embodiment, the beta form is characterized by reflections in the X-Ray powder diffractogram as measured using CuKα radiation at 2-theta angles: 6.6, 8.9, 10.7, 11.7, 24.4, 30.6. The beta form of Compound I may also be characterized by having reflections in the X-Ray diffractogram as measured using CuKα radiation at 2θ angles: 6.6, 8.9, 10.7, 11.4, 11.7, 13.7, 17.0, 18.5, 18.8, 19.2, 20.3, 24.4, 30.6. The beta form of Compound I may also be characterized by the solid state Carbon-13 NMR spectrum shown in FIG. 8. The beta form of Compound I may also be characterized by the NIR reflectance spectrum shown in FIG. 11. The beta form of Compound I may also be characterized by having a melting point in the range of 209-213° C., preferably about 211° C. The beta form of Compound I may also be characterized by having DSC thermogram substantially in accordance with that shown in FIG. 5. The beta form of Compound I may also be characterized by a DSC thermogram having an endotherm from about 205° C. to about 220° C.

Figure 3:
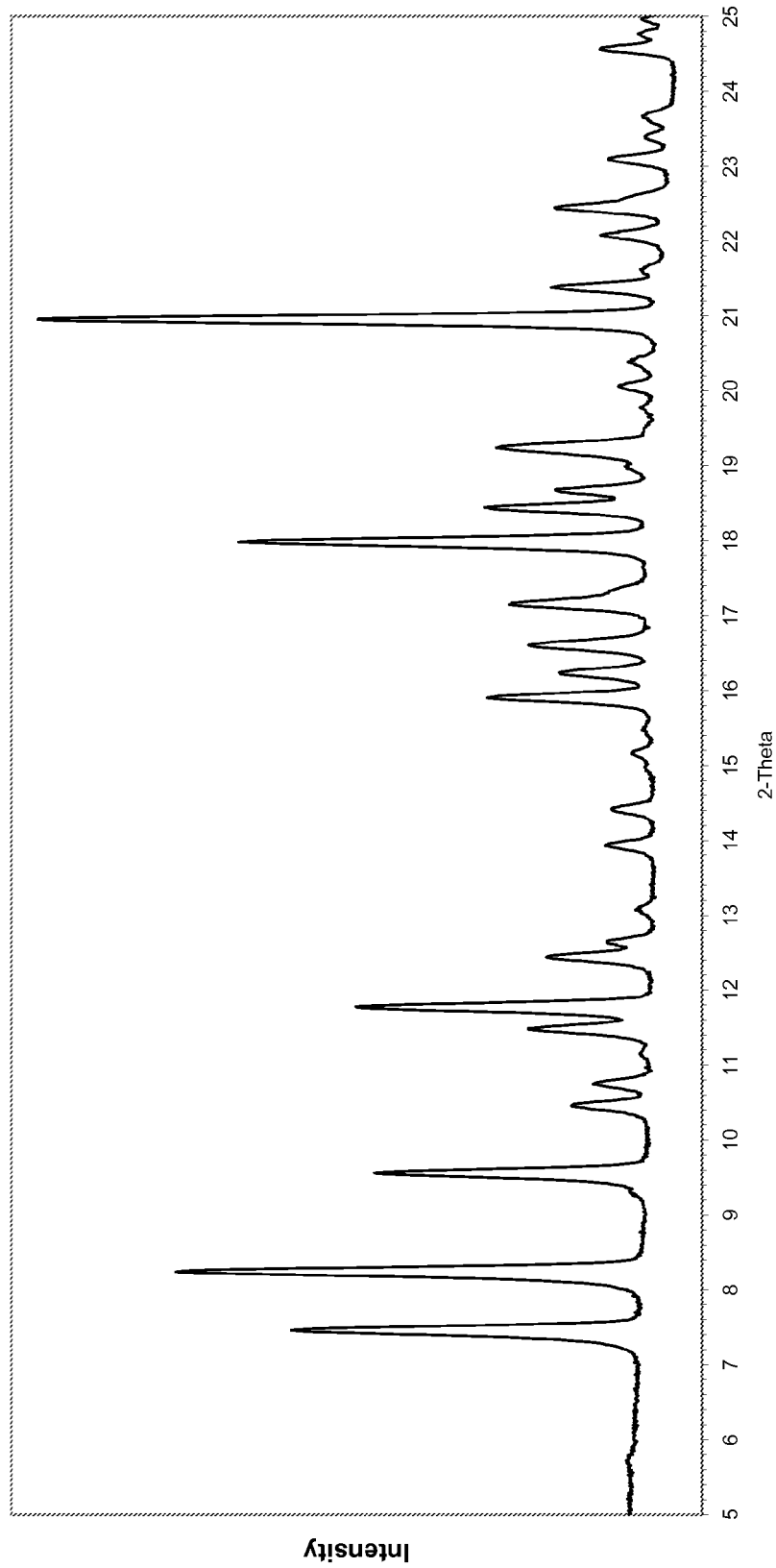
FIG. 3: Shows an x-ray powder diffractogram of Compound I gamma form.
Figure 6:
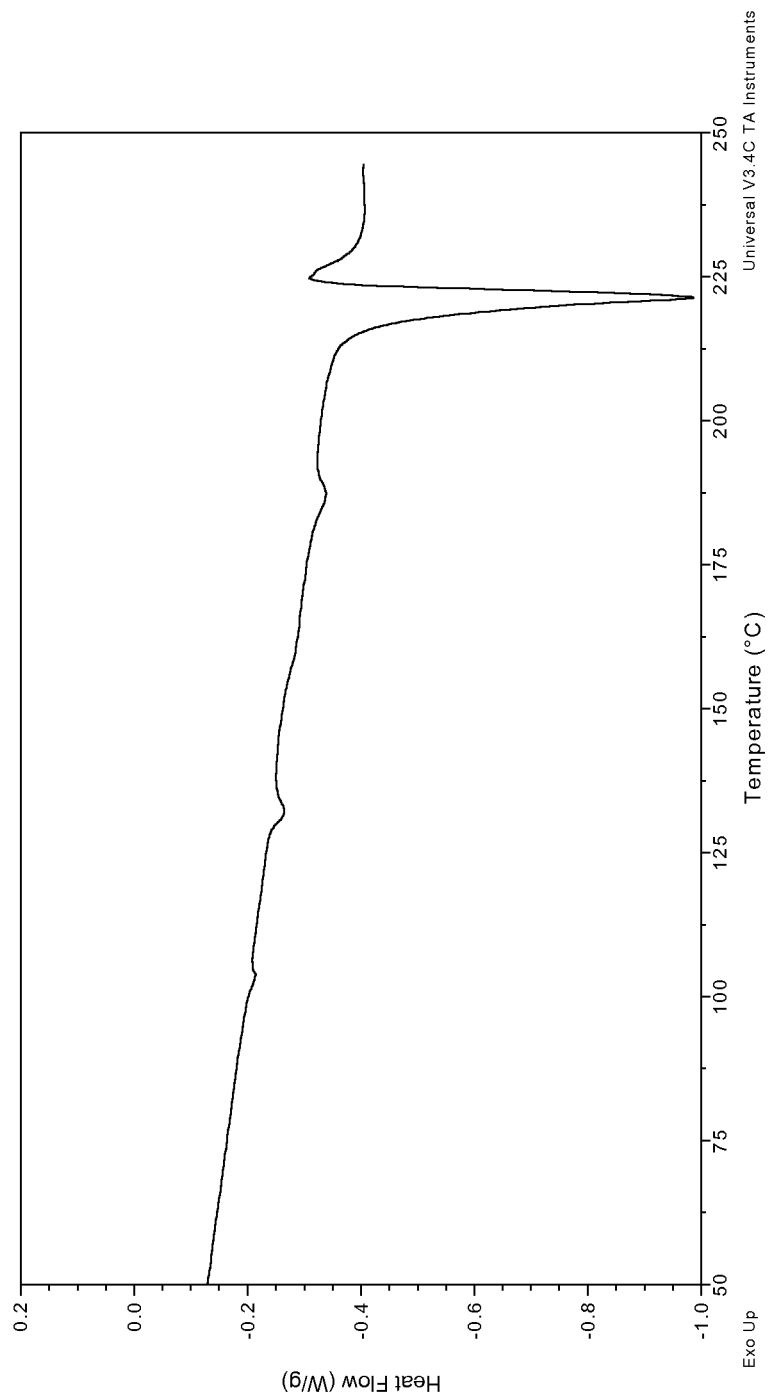
FIG. 6: Shows a DSC thermogram of Compound I gamma form.
Figure 9:
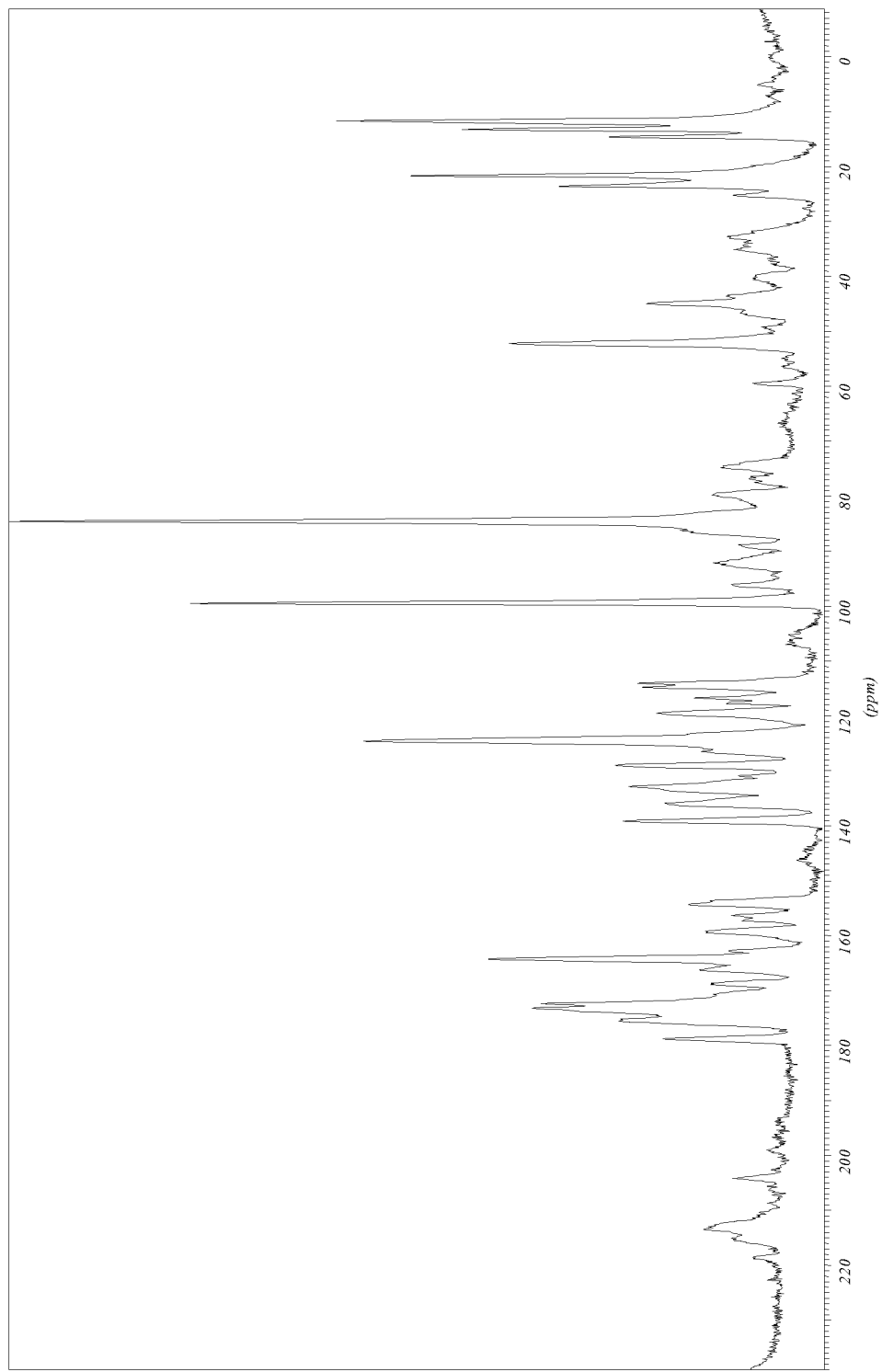
FIG. 9: Shows a solid state Carbon-13 NMR spectrum of Compound I gamma form.
Figure 12:
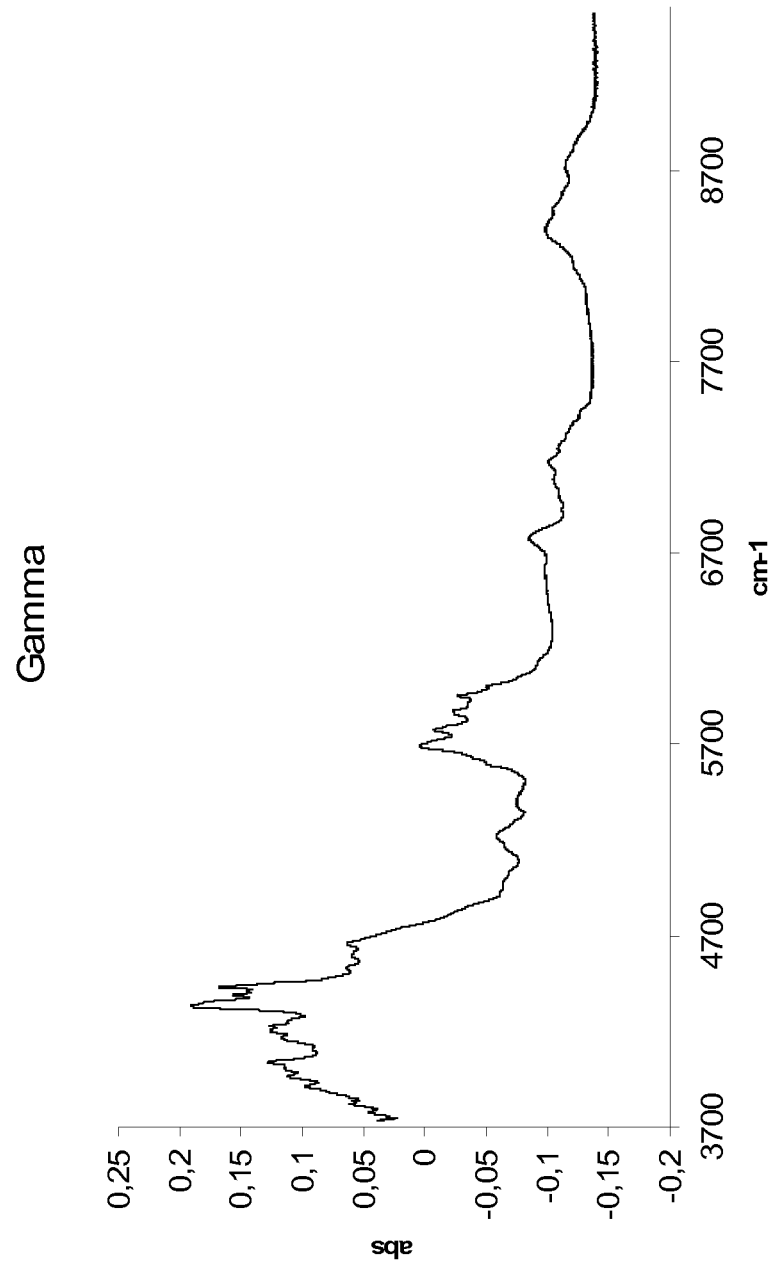
FIG. 12: Shows a NIR reflectance spectrum of Compound I gamma form.

A further embodiment relates to a crystalline form of Compound I named gamma characterized by the X-Ray powder diffractogram shown in FIG. 3 as measured using CuKα radiation. In one embodiment, the gamma form is characterized by reflections in the X-Ray powder diffractogram as measured using CuKα radiation at 2-theta angles: 9.6, 11.5, 12.5, 16.7, 19.3, 28.1. The gamma form of Compound I may also be characterized by having reflections in the X-Ray diffractogram as measured using CuKα radiation at 2θ angles: 7.5, 8.3, 9.6, 11.5, 11.8, 12.5, 15.9, 16.3, 16.7, 17.2, 18.0, 19.3, 21.0, 28.1. The gamma form of Compound I may also be characterized by the solid state Carbon-13 NMR spectrum shown in FIG. 9. The gamma form of Compound I may also be characterized by the NIR reflectance spectrum shown in FIG. 12. The gamma form of Compound I may also be characterized by having a melting point in the range of 212-218° C. The gamma form of Compound I may also be characterized by having DSC thermogram substantially in accordance with that shown in FIG. 6. The gamma form of Compound I may also be characterized by a DSC thermogram having an endotherm from about 210° C. to about 225° C.

Figure 13:
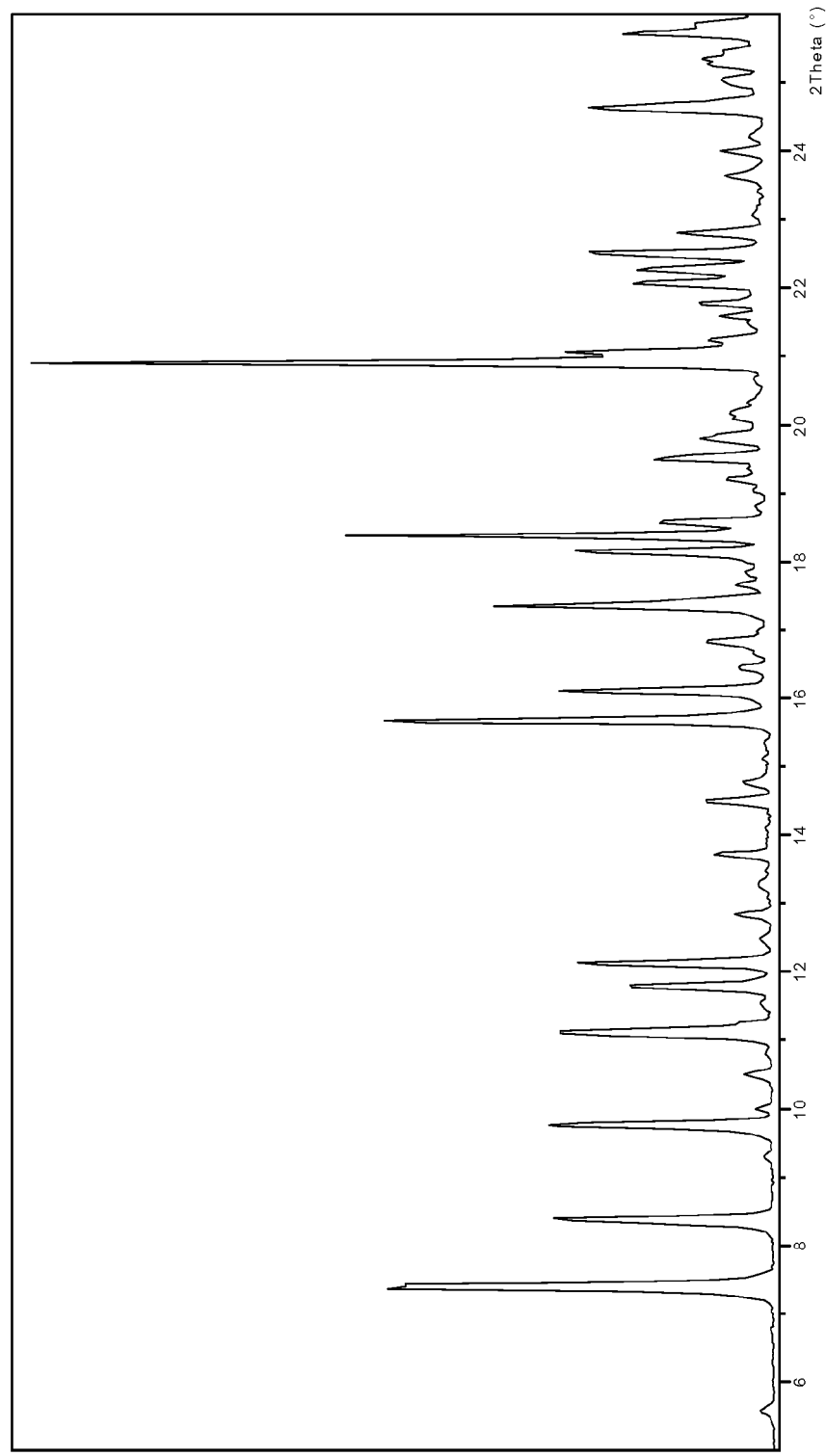
FIG. 13: Shows an x-ray powder diffractogram of Compound I delta form.
Figure 14:
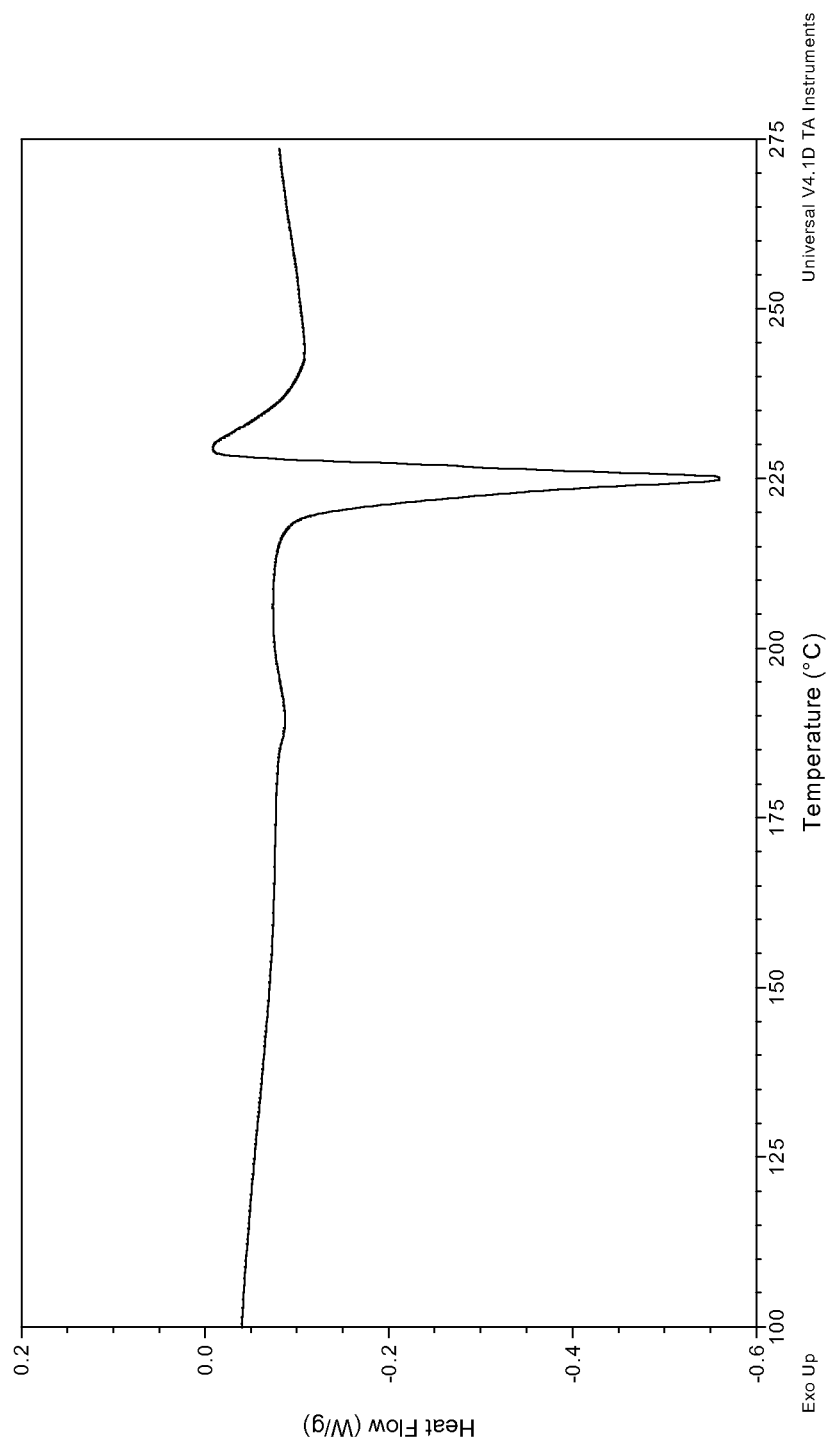
FIG. 14: Shows a DSC thermogram of Compound I delta form.

A further embodiment relates to a crystalline form of Compound I named delta characterized by the X-Ray powder diffractogram shown in FIG. 13 as measured using CuKα radiation. In one embodiment, the delta form is characterized by reflections in the X-Ray powder diffractogram as measured using CuKα radiation at 2-theta angles: 9.7, 12.1, 16.1, 18.3, 22.1, 22.2, 25.7, 25.8. The delta form of Compound I may also be characterized by having reflections in the X-Ray diffractogram as measured using CuKα radiation at 2θ angles: 7.3, 8.3, 9.7, 11.1, 11.7, 12.1, 15.6, 16.1, 17.3, 18.3, 20.9, 22.1, 22.2, 25.7, 25.8. The delta form of Compound I may also be characterized by having a melting point in the range of 211-223° C. The delta form of Compound I may also be characterized by having DSC thermogram substantially in accordance with that shown in FIG. 14. The delta form of Compound I may also be characterized by a DSC thermogram having an endotherm from about 210° C. to about 228° C.

Figure 15:
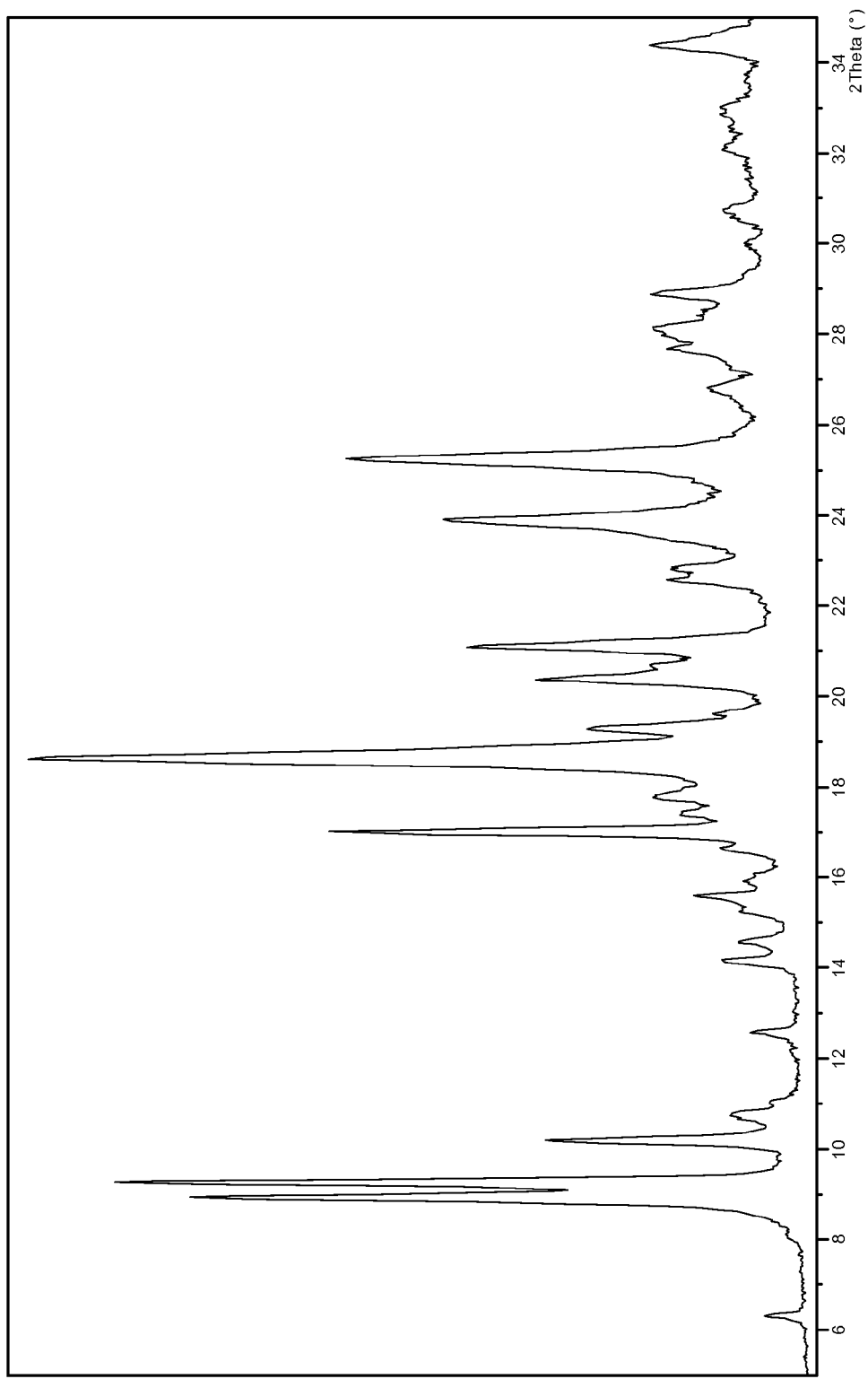
FIG. 15: Shows an x-ray powder diffractogram of Compound I epsilon form.
Figure 16:
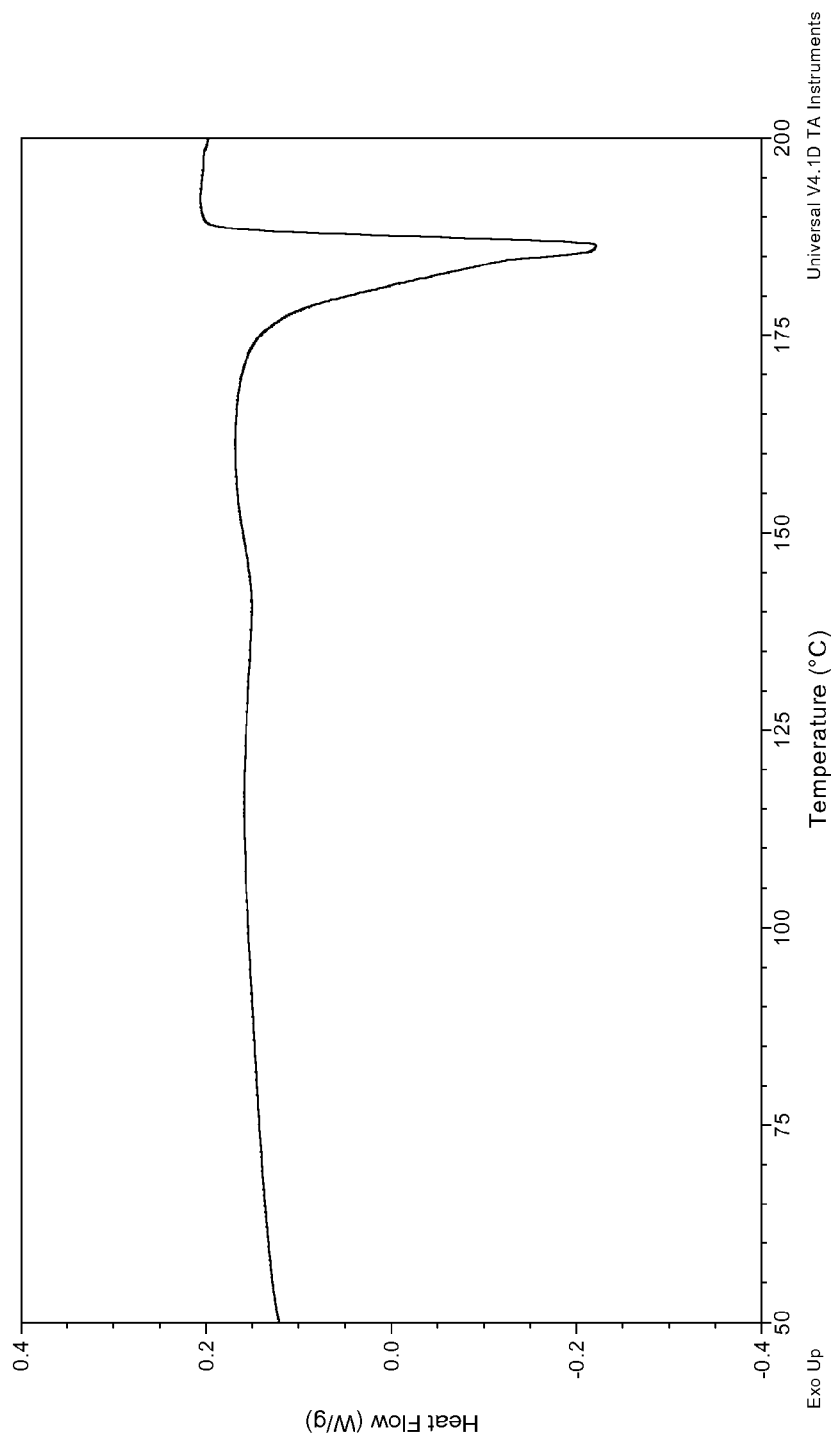
FIG. 16: Shows a DSC thermogram of Compound I epsilon form.

A further embodiment relates to a crystalline form of Compound I named epsilon characterized by the X-Ray powder diffractogram shown in FIG. 15 as measured using CuKα radiation. In one embodiment, the epsilon form of Compound I is characterized by reflections in the X-Ray powder diffractogram as measured using CuKα radiation at 2-theta angles: 8.9, 9.2, 10.2, 14.6. The epsilon form of Compound I may also be characterized by having reflections in the X-Ray diffractogram as measured using CuKα radiation at 2θ angles: 8.9, 9.2, 10.2, 12.6, 14.2, 14.6, 17.0, 18.6, 20.4, 21.1, 23.9, 25.2. The epsilon form of Compound I may also be characterized by having a melting point in the range of 180-185° C. The epsilon form of Compound I may also be characterized by having DSC thermogram substantially in accordance with that shown in FIG. 16. The epsilon form of Compound I may also be characterized by a DSC thermogram having an endotherm from about 175° C. to about 190° C.

The invention further relates to any mixtures of the crystalline forms of the invention, e.g. a mixture of the alpha and gamma crystalline form of Compound I.

As used herein expressions like "crystalline form of Compound I characterized by the X-Ray powder diffractogram shown in FIG. 1) as measured using CuKα" mean the crystalline form of Compound I having an X-ray powder diffractogram substantially similar to FIG. 1, i.e. exhibiting an X-ray powder diffraction pattern as exemplified in that Figure and measured under comparable conditions as described in Example 7.1 or by any comparable method using CuKα radiation. This definition also applies mutatis mutandis to the NMR and NIR Figures, and all other X-Ray data described herein (e.g. X-Ray peak data) and for all of the five crystal forms identified, i.e. alpha, beta, gamma, delta and epsilon, respectively, such that margins of analytical variations are taken into consideration.

The solid state Carbon-13 NMR spectra referred to herein is preferably measured using a sample spinning speed of 5000 Hz on a spectrometer with a CP-MAS probe. Thus, the NMR spectrum is preferably provided as described in Example 7.2 or by any comparable method. The NIR reflectance spectra referred to herein is preferably provided as described in Example 7.3 or by any comparable method, in particular with a resolution 2 cm$^{-1}$ and correction of baseline shift and slope with Multiplicative Scatter Correction (MSC).

In further embodiments, the invention relates to a crystalline form of Compound I, which is substantially pure. The term "substantially pure", as used herein, means that the crystalline form of Compound I, e.g. the alpha, beta, gamma, delta or epsilon form, is having a purity of at least about 90% including, e.g., at least about 93%, and at least about 95%.

The amorphous form of Compound I melts at a temperature about 150° C. which is easy to distinguish from the melting points of the herein described crystalline forms of Compound I, cf. Table 1 in Example 9. Accordingly, within the invention is also crystalline Compound I having a melting point which is at least 175° C., or at least 180° C., such as in the range of 175° C.-225° C., 180° C.-225° C., 180° C.-220° C., or 181° C.-218° C., alternatively in the range of 180° C.-190° C. or 210-225° C.

The term "melting point" as used herein means the onset value of the melting endotherm as measured by DSC, cf. Example 7.4.

A further embodiment, relates to solid Compound I containing crystalline Compound I alpha form. The invention also relates to solid Compound I consisting mainly of the crystalline alpha form of Compound I described herein. The term "mainly" in the present context means that the solid Compound I consists of at least 75%, such as at least 80%, at least 90%, or at least 95% crystalline alpha form of the total Compound I present.

A further embodiment relates to solid Compound I containing crystalline Compound I beta form. The invention also relates to solid Compound I consisting mainly of the crystalline beta form of Compound I described herein. The term "mainly" in the present context means that the solid Compound I consists of at least 75%, such as at least 80%, at least 90%, or at least 95% crystalline beta form of the total Compound I present.

A further embodiment relates to solid Compound I containing crystalline Compound I gamma form. The invention also relates to solid Compound I consisting mainly of the crystalline gamma form of Compound I described herein. The term "mainly" in the present context means that the solid Compound I consists of at least 75%, such as at least 80%, at least 90%, or at least 95% crystalline gamma form of the total Compound I present.

A further embodiment relates to solid Compound I containing crystalline Compound I delta form. The invention also relates to solid Compound I consisting mainly of the crystalline delta form of Compound I described herein. The term "mainly" in the present context means that the solid Compound I consists of at least 75%, such as at least 80%, at least 90%, or at least 95% crystalline delta form of the total Compound I present.

A further embodiment relates to solid Compound I containing crystalline Compound I epsilon form. The invention also relates to a solid Compound I consisting mainly of the epsilon form of Compound I described herein. The term "mainly" in the present context means that the solid Compound I consists of at least 75%, such as at least 80%, at least 90%, or at least 95% crystalline epsilon form of the total Compound I present.

Broadly speaking, the novel crystalline forms of Compound I may be prepared by a variety of methods, including but not limited to crystallizing Compound I from a suitable solvent. Compound I may be prepared using methods known in the art, such as those described herein. By way of general guidance, Compound I may be mixed with a suitable solvent which may be heated to facilitate the dissolution of Compound I. The combination of solvent and Compound I may also be heated to facilitate assist the subsequent conversion to the crystalline form. Preferred temperatures in this regard may range from about 30° C. to about the boiling point (i.e., the reflux temperature) of the solvent. More preferred temperatures may range from about 60° C. to about the boiling point of the solvent. The resulting mixture of solvent and Compound I may be cooled to initiate and/or continue crystallization. The mixture is preferably cooled (i.e. including natural cooling to ambient temperature) to a temperature which ranges from, e.g., about minus 20° C. to about 20° C., e.g. to ambient temperature. The precipitated solids may be isolated from the cooled mixture by for example filtration or centrifugation, and if necessary washed with a suitable solvent such as, but not limited to, the solvent employed for the crystallization, and dried in vacuo at ambient or slightly elevated temperature, e.g. under a nitrogen purge.

Seed crystals may be added to any crystallization mixture to promote crystallization.

As indicated above crystalline Compound I, in particular the different crystal forms of the invention may be prepared by (a) dissolving Compound I in a suitable solvent, (b) crystallizing by precipitation Compound I from the solvent, and (c) separating the solvent from the obtained crystalline Compound I; or alternatively by a process comprising the steps of: (a) suspending Compound I in suitable solvent for a period of time sufficient to convert it into the crystalline form, and (b) separating the alcohol from the obtained crystalline Compound I. Below is described how different solvents can be used to make the different crystal forms of Compound I, alpha, beta, gamma, delta and epsilon. In a preferred embodiment, the method of the invention for preparing crystalline Compound I, including the alpha, beta, gamma, delta or epsilon form, comprises crystallizing by precipitation Compound I from a suitable solvent and separating the solvent form the obtained crystalline Compound I. It is understood in that when referring herein to the preparation of the different crystal forms of the invention, and a product obtainable or more specifically a product obtained by such methods this also applies to "a solid Compound I containing crystalline Compound I", in particular as described above "a solid Compound I consisting mainly of one particular crystalline form of Compound I", e.g. the alpha, beta, gamma, delta or epsilon form.

Accordingly, in one aspect the invention relates to a method for preparing crystalline Compound I, characterised in that said crystalline Compound I is formed in a solvent selected from the group consisting of: (i) methanol with 0% to about 8% water; (ii) an aliphatic $C_3$-$C_6$ alcohol (e.g. 1-propanol, 1-butanol, 2-butanol, tert-butanol, 1-pentanol) with 4-8% water (e.g. 1-butanol with 4% water; 1-propanol with 4% water, 1-pentanol with 4% water, tert-butanol with 7% water, 2-butanol with 4% water); (iii) an ester of acetic acid with at least 4% water present, wherein said ester of acetic acid is defined by the formula $CH_3CO_2R$, where R is a $C_1$-$C_6$-alkyl, e.g. ethyl acetate or isopropyl acetate (e.g. ethyl acetate with 4% water or isopropyl acetate with 6% water). The invention also relates to the crystalline Compound I obtainable, in particular obtained, by such method. In a preferred embodiment, this method leads to the formation of crystalline Compound I alpha form.

In a further aspect, the invention relates to a method for preparing crystalline Compound I, characterised in that said crystalline Compound I is formed in the solvent isopropyl acetate. The invention also relates to the crystalline Compound I obtainable, in particular obtained, by such method. In a preferred embodiment, this method leads to the formation of crystalline Compound I beta form.

In a further aspect, the invention relates to a method for preparing crystalline Compound I, characterised in that said crystalline Compound I is formed in a solvent selected from the group consisting of: (i) an aliphatic $C_1$-$C_3$ nitrile (e.g. acetonitrile, propionitrile) with up to about 12% water (e.g. propionitrile with 4% water or acetonitrile with 12% water), it is understood that propionitrile ($CH_3CH_2CN$) is a $C_3$-nitrile; (ii) ethanol with 0% to about 8% water: (iii) an aliphatic $C_3$-$C_6$ alcohols (e.g. 1-propanol or 1-butanol) with at least about 10% water (e.g. 1-propanol 10% water, 1-butanol 10% water); (iv) ethyl acetate reagent grade. By the term "ethyl acetate reagent grade" is meant less than 0.5% water. The invention also relates to the crystalline Compound I obtainable, in particular obtained, by such method. In a preferred embodiment, this method leads to the formation of crystalline Compound I gamma form.

In a further embodiment, the invention relates to a method for preparing crystalline Compound I, characterised in that said crystalline Compound I is formed in a solvent selected from the group consisting of: (i) an aliphatic $C_2$-$C_6$ alcohol (e.g. ethanol, cyclopropylmethanol or 1 propanol) with less than 4% water, e.g. less than 3%, e.g. about 2% (e.g. cyclopropyl methanol, 1 propanol 2% water, ethanol 2% water (with no stirring). The invention also relates to the crystalline Compound I obtainable, in particular obtained, by such method. In a preferred embodiment, this method leads to the formation of crystalline Compound I delta form.

In a further embodiment, the invention relates to a method for preparing crystalline Compound I, characterised in that said crystalline Compound I is formed in the solvent butyl nitrile ($CH_3CH_2CH_2CN$). The invention also relates to the crystalline Compound I obtainable, in particular obtained, by such method. In a preferred embodiment, this method leads to the formation of crystalline Compound I epsilon form.

It has also been found that each of the crystalline form alpha and beta can be converted to the crystalline gamma form, in the presence of a suitable solvent, in particular acetonitrile as shown in Example 6.1. The crystalline beta form can be converted to the crystalline alpha form in the presence of methanol as shown in Example 6.1.

The invention also relates to a crystalline product, in particular the crystalline forms of Compound I obtainable, or in a preferred embodiment obtained, by a process described herein for the preparation of Crystalline Compound I.

The invention in a further aspect relates to a process for the preparation of Compound I comprising converting a crystalline form of Compound I (e.g. the alpha, beta or gamma form as described herein or any mixtures hereof) into the amorphous form of Compound I. Such process in a preferred embodiment comprises the steps of: (a) dissolving crystalline Compound I in an aromatic solvent, i.e. an aromatic hydrocarbon, preferably an alkyl-benzene such as xylene or toluene, (b) precipitating Compound I from the aromatic solvent; and (c) separating the aromatic solvent from the precipitated amorphous Compound I.

As indicated above the formation of crystalline Compound I is very useful inter alia as a purification step in the manufacturing of Compound I for pharmaceutical use.

The invention in one aspect relates to a process for the manufacturing of Compound I comprising a crystallization step as described herein. Thus, one embodiment of the invention relates to a method for the manufacturing of Compound I, which method comprises a step wherein Compound I is converted to crystalline Compound I. It is understood that the crystalline Compound I of the invention may be prepared by a method as described herein, e.g. by precipitating Compound I in crystalline form from a solvent as described herein and separating the obtained crystalline Compound I from the solvent.

The invention in particular relates to method for the manufacturing of Compound I wherein the Compound I is converted to crystalline Compound, including a crystalline form of the invention, e.g. the alpha or gamma form from a crude mixture of Compound I. The term crude mixture in this context means that the mixture comprises impurities, e.g. oxidation products derived from Compound I which it is desired to remove. The crude mixture may be separated directly from the reaction mixture, or the crude reaction mixture may have been subjected to some initial purification, e.g. treating with a base. The invention further relates to the use of a crystalline Compound I or a solid of the invention in the preparation of a medicament comprising Compound I as an active ingredient.

Accordingly, the invention also relates to a method for the manufacturing of a pharmaceutical composition of Compound I, which method comprises preparing said composition from crystalline Compound I as defined herein, e.g. obtained by a method as described herein, including a crystalline form or a solid of the invention. One specific embodiment relates to such use of the alpha or gamma form of the invention for the preparation of a pharmaceutical composition. As described earlier, preparing the formulations from a defined crystal form has the advantage of improved purity and yield and by having well defined properties, such as solubility. In this respect, the invention also provides a pharmaceutical composition comprising an effective amount of Compound I obtainable or obtained by a method of the invention for the preparation of crystalline Compound I, including a crystalline form of the invention, e.g. from the alpha or gamma form. The pharmaceutical composition may be any composition found suitable for administration of Compound I, e.g. a solid dispersion formulation or a solid solution formulation.

In one embodiment, the crystalline product of the invention, i.e. including in particular the alpha, beta, gamma, delta or epsilon crystalline form, or mixtures thereof, may be formulated into a solid solution or a solid dispersion. A solid solution may be prepared by dissolving the crystalline product of the invention in a molten vehicle. The solid solution is formed upon cooling to ambient temperature. A solid dispersion may be prepared by dispersing the crystalline product of the invention in a molten vehicle. The solid dispersion is formed upon cooling to ambient temperature. The vehicle used to prepare the solid solution or solid dispersion may be one component or a mixture of more components. The vehicle used to prepare the solid solution or the solid dispersion is normally solid or semi-solid at room temperature and normally it has a sticky, oily or waxy character. However, the vehicle may also be fluid at room temperature or even at temperature below 5° C. As examples of vehicles can be mentioned polyethylene glycols (PEG), poloxamers, esters of polyethylene glycols, waxes, glycerides, fatty acid alcohols, fatty acids, sugar alcohols, vitamin E and derivatives of vitamin E. The solid solution or solid dispersion may be used as is or alternatively formulated into pharmaceutical compositions like tablets, capsules etc. The solid solution and solid dispersion can also be prepared by other methods as for example by the solvent method or the fusion method (Serajuddin, A. T. M., Journal of Pharmaceutical Sciences, Vol. 88, 1058-1066). One embodiment of the invention relates to a pharmaceutical composition which is a solid solution made from crystalline Compound I of the invention, e.g. from the crystalline alpha or gamma form of the invention.

Thus, the crystalline product of the invention, in particular the alpha, beta, gamma, delta or epsilon crystalline forms, or mixtures thereof can be used in the preparation of a pharmaceutical composition with Compound I in solution, e.g. a composition similar to those disclosed in U.S. Pat. No. 6,200,968.

Within the invention is also a pharmaceutical composition comprising an effective amount of crystalline Compound I as described herein, in particular the alpha, beta, gamma, delta or epsilon forms defined herein or mixtures thereof, and a pharmaceutically acceptable carrier.

The crystalline product of the invention, i.e. including the crystalline alpha, beta, gamma, delta or epsilon form, or mixtures thereof, may be formulated into a variety of pharmaceutical compositions. Examples of such formulations comprising a crystalline product of the invention (e.g. crystalline alpha, beta, gamma, delta or epsilon forms) are tablets, capsules, granules, powders, suppositories and suspensions. The expression "crystalline product of the invention" means a crystalline Compound I or a solid Compound I as described herein, i.e. by "solid Compound I" is in the present context understood a solid Compound I consisting mainly of crystalline Compound I as compared to amorphous Compound.

The pharmaceutical compositions according to the invention may be formulated with pharmaceutically acceptable carriers or diluents as well as any other adjuvants and excipients, e.g. in accordance with techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

In an embodiment of the pharmaceutical composition, Compound I is administered in an amount of from about 0.001 to about 100 mg/kg body weight per day. Compound I may, e.g. be administered in a unit dosage form containing said compound in an amount of about 0.01 to 100 mg. The total daily dose is, e.g., in the range of about 0.05-500 mg. The formulations may conveniently be presented in unit dosage form by methods known to those skilled in the art. A typical unit dosage form for oral administration one or more times per day such as 1 to 3 times per day may contain from 0.01 to about 1000 mg, preferably from about 0.05 to about 500 mg. For parenteral routes such as intravenous, intrathecal, intramuscular and similar administration, typically doses are in the order of about half the dose employed for oral administration.

As indicated above, the following embodiments are within the invention: Crystalline Compound I for use as a medicament; the crystalline alpha form for use as a medicament; the crystalline beta form for use as a medicament; the crystalline gamma form for use as a medicament, the crystalline delta form for use as a medicament; the crystalline epsilon form for use as a medicament.

The invention further relates to the use of crystalline Compound I as described herein e.g. the alpha, beta, gamma, delta or epsilon form defined herein or mixtures thereof, in the preparation of a medicament for the treatment of a CNS disease, e.g., for treatment of a neurodegenerative disease, such as, e.g., Parkinson's disease, Alzheimer's disease, Huntington's disease, peripheral neuropathy, AIDS dementia, or ear injuries including noise-induced hearing loss.

Similarly, within the invention is also a method for treating a neurodegenerative disease, such as e.g. Parkinson's disease, Alzheimer's disease, Huntington's disease, peripheral neuropathy, AIDS dementia, or ear injuries including noise-induced hearing loss, comprising administering a pharmaceutically effective amount of crystalline Compound I as described herein, e.g. the alpha, beta, gamma form, delta or epsilon defined herein or mixtures thereof.

The above medical uses and pharmaceutical compositions, e.g. for treatment of Parkinson's disease, of crystalline Compound I and a crystalline form of the invention, is likewise applicable to the solid Compound I defined herein as comprising a crystalline form of the invention, in particular a solid Compound I consisting mainly of a crystalline form of the invention.

The term "treatment" in connection with a disease as used herein also includes prevention as the case may be. The term "disease" as used herein also includes a disorder as the case may be.

The invention disclosed herein is further illustrated by the following non-limiting examples.

EXAMPLES

In the following the starting material "Compound I" may, e.g., be prepared as described by Kaneko M. et al in J. Med. Chem. 1997, 40, 1863-1869.

Example 1

Preparation of Crystalline Alpha Form of Compound I

Method I):

6.0 g amorphous Compound I was dissolved in 30 ml acetone. 0.6 g potassium carbonate was added and the suspension was stirred at room temperature for 1 hour before it was filtered to remove potential minor insoluble impurities and inorganic salts. The filter cake was washed with acetone. The filtrate was then evaporated on a rotary evaporator under reduced pressure at 60° C. to a final volume of 10 ml to which 100 ml methanol was added slowly. The product separated as an oil, which almost dissolved on heating to reflux. Subsequently the residual insoluble impurities were removed by filtration. The filtrate was left with stirring at room temperature. A crystalline solid separated and was isolated by filtration. The filter cake was washed with methanol and dried in vacuo at 60° C. overnight. Yield 2.83 g (47%), mp=182.4° C. (DSC onset value), Weight loss by heating: 0.5%, Elemental analysis: 6.71% N, 63.93% C, 5.48% H, theoretical values corrected for 0.5% $H_2O$: 6.79% N, 64.05% C, 5.43% H. XRPD analysis conforms with the alpha form.

Method II):

5 g amorphous Compound I was dissolved in 25 ml acetone by gentle heating. 10 ml Methanol was added very slowly until the solution got turbid. The solution was allowed to cool to room temperature by natural cooling. The suspension was filtered and the filter-cake discarded. During filtration more material precipitated in the filtrate. The filtrate was heated until all material redissolves. Cold methanol was then added to the solution until precipitation was observed. The slightly turbid solution was then heated until all material was in solution. The solution was allowed to cool to room temperature, and the precipitate was removed by filtration. The second filter-cake was discarded. During the filtration some material separated in the filtrate. Heating redissolved the beginning crystallisation in the filtrate. Cold methanol was then added to the solution until precipitation was observed. The suspension was heated until a clear solution was obtained. The solution was allowed to reach room temperature by natural cooling. After a short period of time (15 min) precipitation begun. The precipitated pale yellow product was isolated by filtration and dried in vacuo at 50° C. overnight.

mp=188.9° C. (DSC onset value), Weight loss by heating: 0.3%, Elemental analysis: 6.53% N, 64.33% C, 5.43% H, theoretical values: 6.82% N, 64.37% C, 5.37% H. XRPD analysis conforms with the alpha form.

Method III:

0.5 g Compound I in a mixture of isopropyl acetate (10 mL) and water (0.6 mL) was heated to reflux with stirring. The compound was not completely dissolved so isopropyl acetate (10 mL) and water (0.6 mL) were added and heated to reflux. Stirring was stopped and the experiment was allowed to cool to room temperature. The crystalline product obtained were isolated by filtration and dried in vacuo at 40° C. Yield=0.25 g, mp=183.7° C. (DSC onset value). XRPD analysis conforms with the alpha form.

Method IV:

0.5 g Compound I in a mixture of ethyl acetate (10 mL) and water (0.4 mL) was heated to 70° C. with stirring. The experiment was allowed to cool to room temperature. The crystalline product obtained were isolated by filtration and dried in vacuo at 40° C. XRPD analysis conforms with the alpha form.

Example 2

Preparation of Crystalline Beta Form of Compound I 28.0 g amorphous Compound I was dissolved in 250 ml tetrahydrofuran (THF) and evaporated onto 60 g silica gel. The compound was purified by column chromatography on silica gel (Ø: 10 cm h: 5 cm with 2.7 l THF/heptane 2/1). The eluent containing the desired compound was evaporated a rotary evaporator at reduced pressure at 50° C. to a solid (26 g). The solid was suspended in 600 ml isopropyl acetate and the suspension heated to reflux until almost all material was dissolved. The suspension was cooled on a water/ice bath. The cold suspension was filtered, and the filter cake was washed with isopropyl acetate and dried in vacuo overnight at 50° C.

Yield: 16.9 g (61%), mp=211.7° C. (DSC onset value), Weight loss by heating: 0.2%, Elemental analysis: 6.59% N, 64.63% C, 5.41% H, theoretical values: 6.82% N, 64.37% C, 5.40% H, XRPD analysis conforms with the beta form.

Example 3

Preparation of Crystalline Gamma Form of Compound I

Method I:

15 g amorphous Compound I was dissolved in 75 ml acetone. 1.5 g potassium carbonate was added and the suspension stirred for 90 minutes. The suspension was filtered. The filtrate was reduced to approximately 30 ml on a rotary evaporator at reduced pressure at 60° C. 150 ml Methanol was added to the reduced filtrate, and some sticky material separated. The suspension was heated to reflux. During the heating all material dissolves. The solution was allowed to cool to room temperature by natural cooling, during this period solid material separated. The suspension was left with stirring at room temperature overnight.

The suspension was filtered and the filter cake washed with methanol. The filter cake was dried in vacuo at 50° C. overnight. Intermediate yield is 10.2 gram (68%).

The dry filter cake was suspended in 100 ml acetonitrile (ACN) and heated to reflux. At reflux a turbid solution was obtained. Additional acetonitrile was added until a clear solution was obtained; in total the filter cake was dissolved in 200 ml acetonitrile including the 100 ml used for suspension.

The solution was cooled to room temperature overnight. The following day the crystalline product was isolated by filtration. The filter cake was washed by a small amount of acetonitrile and dried in vacuo at 55° C. overnight.

Yield: 6.17 g, 41%, mp=218.0° C. (DSC onset value), Weight loss by heating: <0.1%, Elemental analysis: 6.80% N, 64.38% C, 5.43% H, theoretical values: 6.82% N, 64.37% C, 5.40% H, Purity (HPLC, area %): 98.6, XRPD analysis conforms with the gamma form.

Method II:

0.5 g Compound I in a mixture of acetonitrile (8.8 mL) and water (1.2 mL) was heated to 70 C with stirring. The solution was allowed to cool slowly to room temperature. The next day the crystalline product was isolated by filtration and dried in vacuo at 40° C., mp=214.2° C. (DSC onset value) XRPD analysis conforms with the gamma form.

Method III:

0.5 g Compound I in ethyl acetate (5 mL) was heated to 70° C. with stirring. The solution was allowed to cool slowly to room temperature. After 12 days the crystalline product was isolated by filtration and dried in vacuo at 40° C. XRPD analysis conforms with the gamma form.

Example 4

Preparation of Crystalline Delta Form of Compound I

Method I:

0.5 g alpha form Compound I in cyclopropyl methanol (10 mL) was heated to 70° C. The solution was allowed to cool slowly to room temperature. After 2 days the crystalline compound was isolated by filtration and dried in vacuo at 40° C. Yield=0.24 g, mp=212.1° C. (DSC onset value), XRPD analysis conforms with the delta form.

Method II:

0.2 g alpha form Compound I in ethanol (10 mL) was heated to 70° C. with stirring. The stirring was stopped and the solution was allowed to cool slowly to room temperature. The next day the crystalline product was isolated by filtration and dried in vacuo at 40° C. Yield=0.15 g, mp=221.6° C. (DSC onset value), XRPD analysis conforms with the delta form Method III:

0.5 g Compound I in 1-propanol (15 mL) was heated to 70° C. with stirring. The stirring was stopped and the solution was allowed to cool slowly to room temperature. The next day the crystalline compound was isolated by filtration and dried in vacuo at 40° C. Yield=0.23 g, XRPD analysis conforms with the delta form.

Example 5

Preparation of Crystalline Epsilon Form of Compound I 0.5 g alpha form Compound I in butylnitrile (10 mL) was heated to 70° C. with stirring. The solution was allowed to cool slowly to room temperature. The next day the crystalline product was isolated by filtration and dried in vacuo at 40° C. Yield=0.3 g, mp=181.8° C. (DSC onset value), XRPD analysis conforms with the epsilon form.

Example 6

Transformation Between Different Solid Forms of Compound I 6.1 Conversions to Crystalline Compound I In the following examples are used excess of solid Compound I, i.e. compared to the solvent the amounts of solid Compound I is such that not all the solid material comes into solution. The amounts used varied between 25-50 mg solid Compound I and 2-5 ml solvent. In the present context by "solid Compound I" is meant amorphous Compound I or any of the crystalline forms of Compound I as indicated below.

(i) Excess of amorphous Compound I was added to methanol and the resulting suspension was stored on a rotarmix for 4 days at room temperature. After 4 days the solid was the alpha form as determined by powder X-ray diffraction.

(ii) Excess of the crystalline alpha form of Compound I was added to methanol and the resulting suspension was stored on a rotarmix for 4 days at room temperature. After 4 days the solid was still the alpha form as determined by powder X-ray diffraction.

(iii) Excess of the crystalline beta form of Compound I was added to methanol and the resulting suspension was stored on a rotarmix for 4 days at room temperature. After 4 days the solid was the alpha form as determined by powder X-ray diffraction.

(iv) Excess of the crystalline gamma form of Compound I was added to methanol and the resulting suspension was stored on a rotarmix for 4 days at room temperature. After 4 days the solid was still the gamma form as determined by powder X-ray diffraction.

(v) Excess of a 1:1 mixture of the alpha and the gamma form of Compound I was added to methanol and the resulting suspension was stored on a rotarmix stored for 4 days at room temperature. After 4 days the major part of the solid was the gamma form. After filtration the supernatant was left for evaporation of the solvent. The resulting solid was the alpha form as determined by powder X-ray diffraction.

(vi) Excess of amorphous Compound I was added to acetonitrile (ACN) and the resulting suspension was stored on a rotarmix for 4 days at room temperature. After 4 days the solid was the gamma form as determined by powder X-ray diffraction.

(vii) Excess of the crystalline alpha form of Compound I was added to ACN and the resulting suspension was stored on a rotarmix for 4 days at room temperature. After 4 days the solid was the gamma form as determined by powder X-ray diffraction.

(viii) Excess of the crystalline beta form of Compound I was added to ACN and the resulting suspension was stored on a rotarmix for 4 days at room temperature. After 4 days the solid was the gamma form as determined by powder X-ray diffraction.

(ix) Excess of the crystalline gamma form of Compound I was added to ACN and the resulting suspension was stored on a rotarmix for 4 days at room temperature. After 4 days the solid was still the gamma form as determined by powder X-ray diffraction.

Conclusion:

Amorphous Compound I and the crystalline beta form can be converted into crystalline alpha form in a methanol suspension.

Amorphous Compound I, the crystalline alpha form and the crystalline beta form can be converted into the crystalline gamma form by suspension of excess of the solid material in acetonitrile.

6.2 Conversions from Crystalline Alpha Form to Amorphous Compound I 15 g crystalline alpha form of Compound I was heated to reflux in a mixture of Toluene (110 mL) and methanol (1 mL); a clear solution was obtained. Under reduced pressure the solvent volume was decreased by 10 mL and the solution was cooled overnight in a freezer. The resulting solid was isolated by filtration, dried in vacuo over two days at 40° C. to give 13.2 g of a solid. The melting temperature of the solid was approx. 150° C. which characterises the amorphous form of Compound I as compared to the crystalline forms, cf. Table 1 below.

Example 7

Analytical Methods (7.1) XRPD patterns were measured on a Diffractometer under one of the following conditions:

(i) STOE diffractometer

Radiation: Cu(Kα1), germanium monochromator, λ=1.540598 Å

Position Sensitive Detector (PSD) covering 7°

Scan type: Step scan, steps: 0.1°, 125-150 sec. pr. step

Range: 5-45°2θ

Sample measuring method: Transmission (ii) PANalytical X'Pert PRO X-Ray Diffractometer using CuK$_{α1}$ radiation.

X'celerator detector, measuring the range 5-40°2θ.

Sample measuring method: Reflection (7.2) The solid state NMR was performed under the following conditions:

The Carbon-13 CP/MAS (cross-polarization/magic-angle spinning) NMR spectra were acquired at room temperature at 11.75 Tesla on a Bruker Avance DRX-500 spectrometer equipped with a 4 mm CP/MAS probe. The sample spinning speed was 5000 Hz, and 10240 scans were acquired using a recycle delay of 5 sec. For the cross polarization, spin-lock radio frequency fields of 50 kHz and a contact time of 5 msec were employed.

(7.3) Near-infrared (NIR) data were collected with Bomem MB 160 FT/NIR spectrometer with Powder SamplIR. The NIR reflectance spectra were recorded between 14.000-4.000 cm-1 with resolution 2 cm-1 (16 scans, high gain). Baseline shift and slope in NIR spectra, which is often seen in powder, were removed with Multiplicative Scatter Correction (MSC).

(7.4) Melting points were determined on a DSC (Differential Scanning Calorimeter) as the onset temperature of the melting endotherm. About 2 mg of sample was heated in an aluminium crucible with loose lid, at 5° C./min under $N_2$ flow.

(7.5) The crystal structure of the alpha form was determined under the following conditions: The diffraction data were collected on a Nonius KappaCCD diffractometer. The data collection was performed at 122 K using monochromatized MoK$_\alpha$, radiation ($\lambda$=0.71073 Å).

Example 8

Analytical Results 8.1 X-ray powder data: The X-ray powder diffractogram (XRPD) of; the alpha form is shown in FIG. 1; the beta form is shown in FIG. 2; the gamma form is shown in FIG. 3; the delta form is shown in FIG. 13; the epsilon form is shown in FIG. 15. The different crystalline forms are characterized by different reflections (peaks) in the X-Ray powder diffractogram as measured using CuK$\alpha$ radiation at 2-theta angles determined:

Alpha (5.2, 10.1, 10.4, 13.2, 15.1, 25.1; 5.2, 7.3, 8.1, 10.1, 10.4, 11.2, 13.2, 15.1, 15.5, 17.3, 21.7, 23.8, 25.1);

Beta (6.6, 8.9, 10.7, 11.7, 24.4, 30.6; 6.6, 8.9, 10.7, 11.4, 11.7, 13.7, 17.0, 18.5, 18.8, 19.2, 20.3, 24.4, 30.6);

Gamma (9.6, 11.5, 12.5, 16.7, 19.3, 28.1; 7.5, 8.3, 9.6, 11.5, 11.8, 12.5, 15.9, 16.3, 16.7, 17.2, 18.0, 19.3, 21.0, 28.1);

Delta (9.7, 12.1, 16.1, 18.3, 22.1, 22.2, 25.7, 25.8; 7.3, 8.3, 9.7, 11.1, 11.7, 12.1, 15.6, 16.1, 17.3, 18.3, 20.9, 22.1, 22.2, 25.7, 25.8);

Epsilon (8.9, 9.2, 10.2, 14.6; 8.9, 9.2, 10.2, 12.6, 14.2, 14.6, 17.0, 18.6, 20.4, 21.1, 23.9, 25.2).

8.2. DSC thermograms: The DSC thermograms are shown in FIGS. 4-6, 14, 16 (alpha form in FIG. 4; beta form in FIG. 5; and gamma form in FIG. 6, delta form in FIG. 14, epsilon form in FIG. 16).

Figure 7:
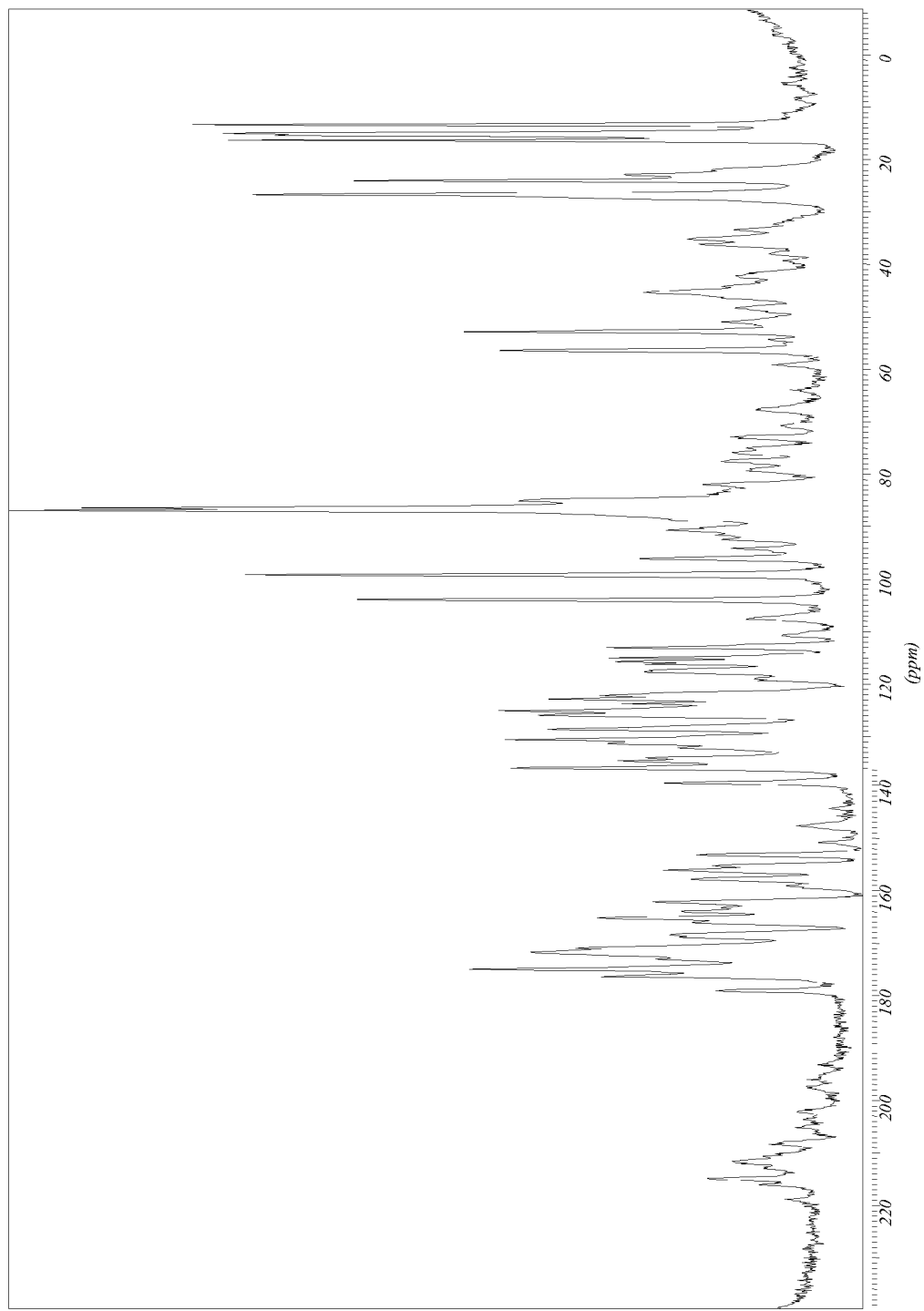
FIG. 7: Shows a solid state Carbon-13 NMR spectrum of Compound I alpha form.

8.3. Solid state NMR data: The solid state NMR spectra are shown in FIG. 7 for the alpha form, FIG. 8 for the beta form and FIG. 9 for the gamma form.

Figure 10:
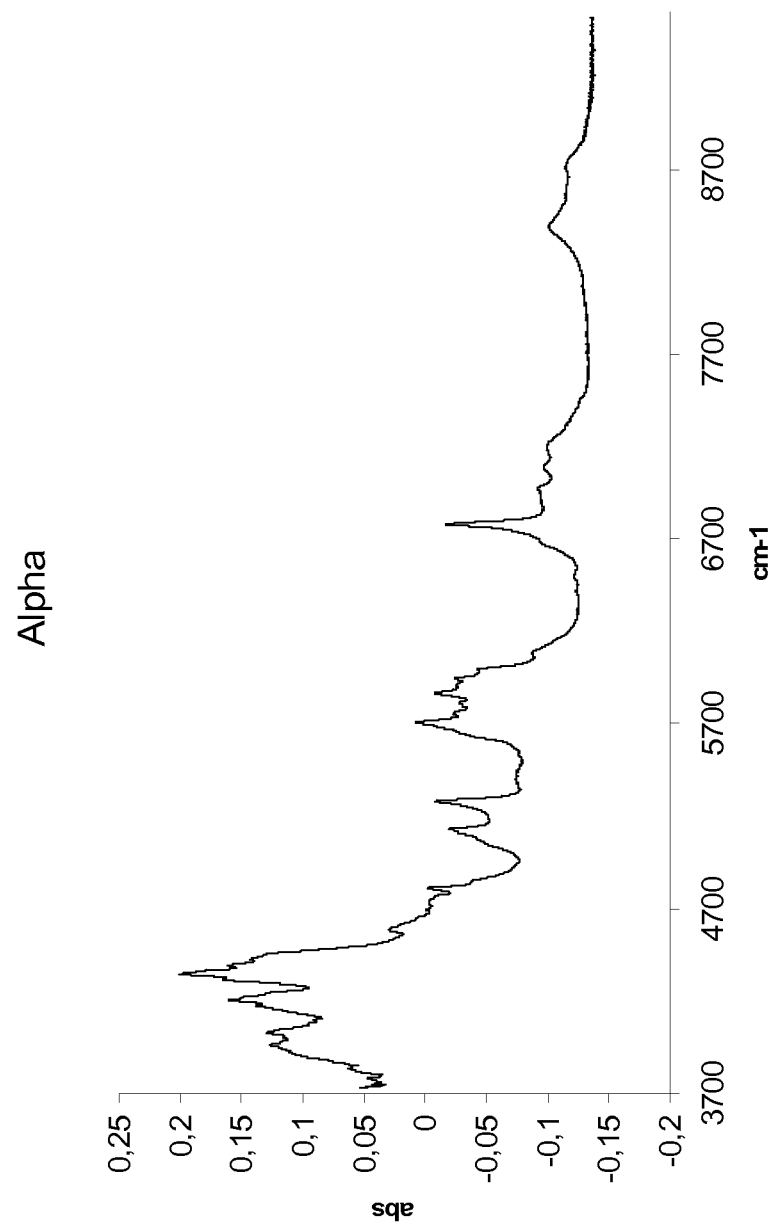
FIG. 10: Shows a NIR reflectance spectrum of Compound I alpha form.

8.4 NIR data: The NIR-spectra are shown in FIG. 10 for the alpha form, FIG. 11 for the beta form and FIG. 12 for the gamma form.

8.5 Crystal structure for Compound I alpha form: The crystal structure of the alpha form was determined by single crystal X-ray diffraction at 122 K. The crystal used for the structure determination was obtained by slow precipitation from MeOH and had dimensions 0.5×0.3×0.2 mm.

The resulting crystal structure shows that the alpha form of Compound I crystallizes in the orthorhombic space group P2$_1$2$_1$2$_1$ with the cell dimensions at 122 K of: a=10.227(2) Å, b=23.942(2) Å and c=24.240(2) Å, $\alpha$=90°, $\beta$=90°, $\gamma$=90°, V=5935.3(12) Å$^3$, Z=8, density=1.378 g/cm$^3$ (the numbers in parenthesis are standard deviations on the last digit). The un-weighted agreement factor was R[I>2$\sigma$(I)]=0.0699.

Figure 17:
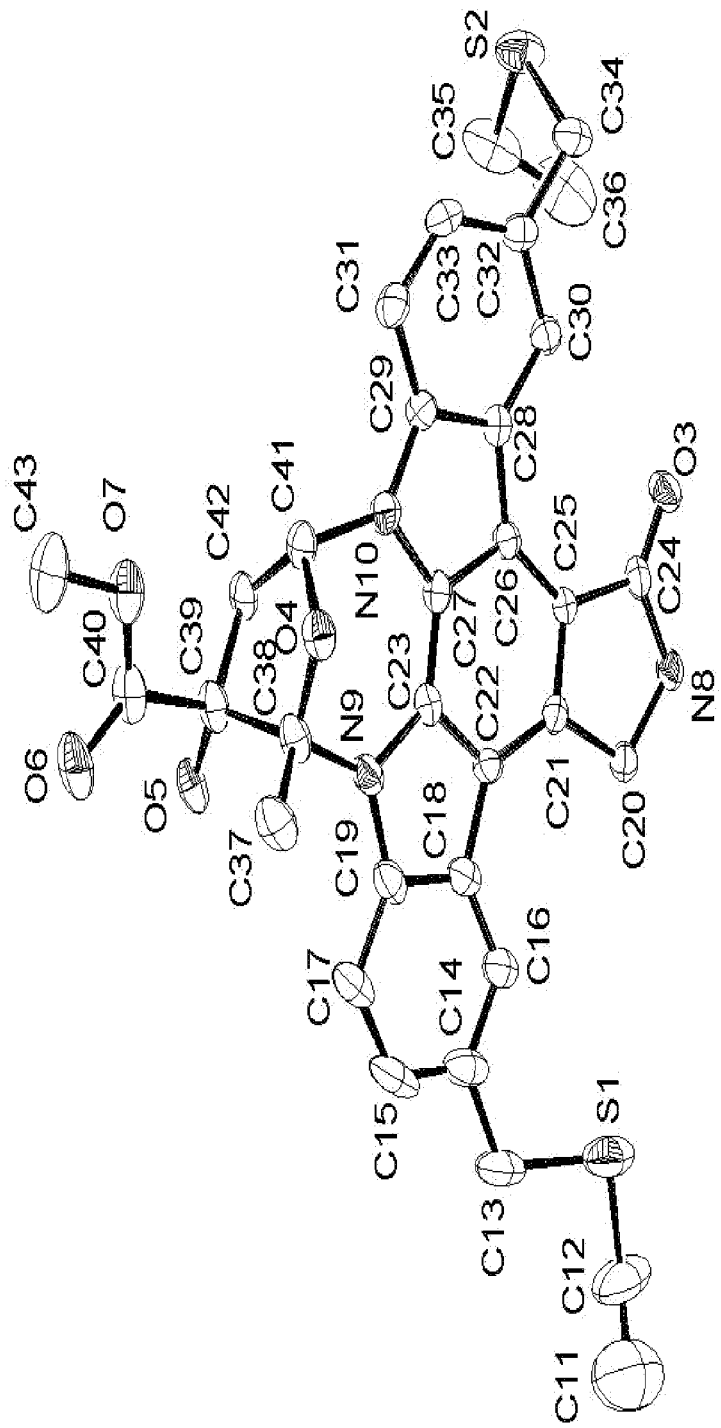
FIG. 17: Shows the conformation of one of the molecules (molecule 1) in Compound I alpha form.
Figure 18:
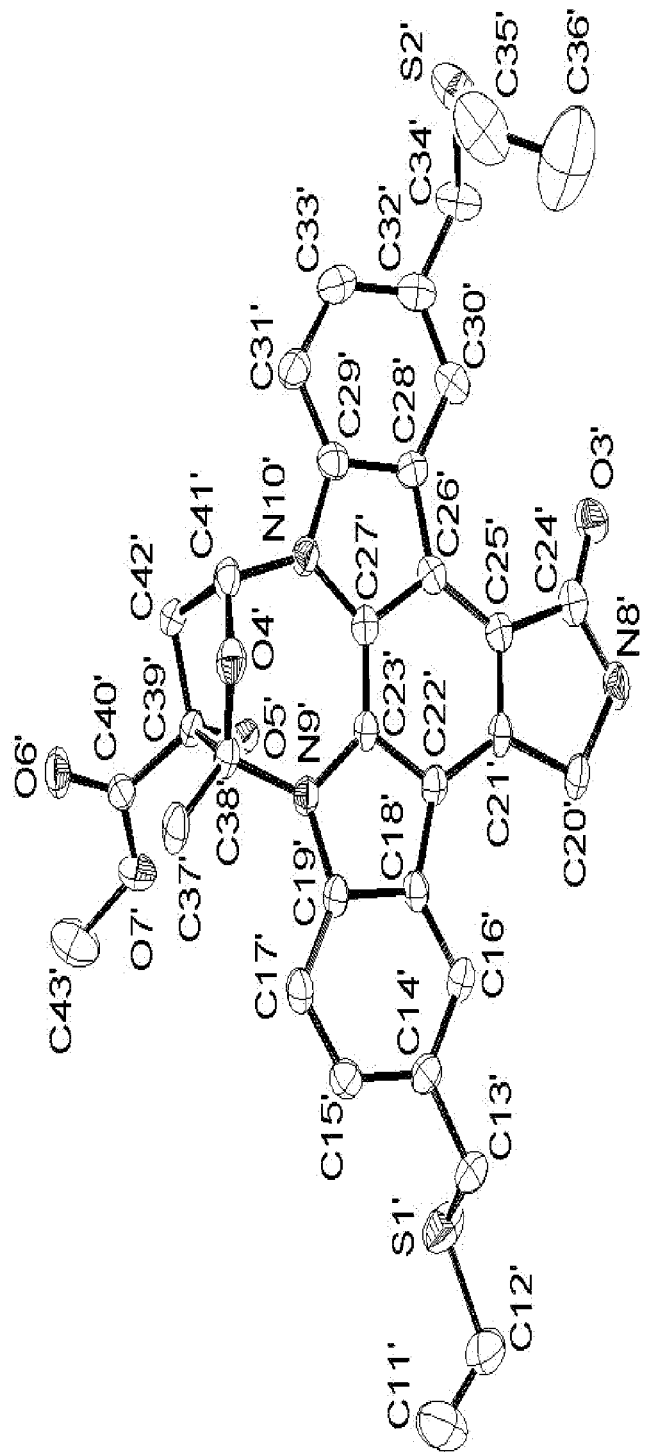
FIG. 18: Shows the conformation of the other molecule (molecule 2) in Compound I alpha form.
Figure 19:
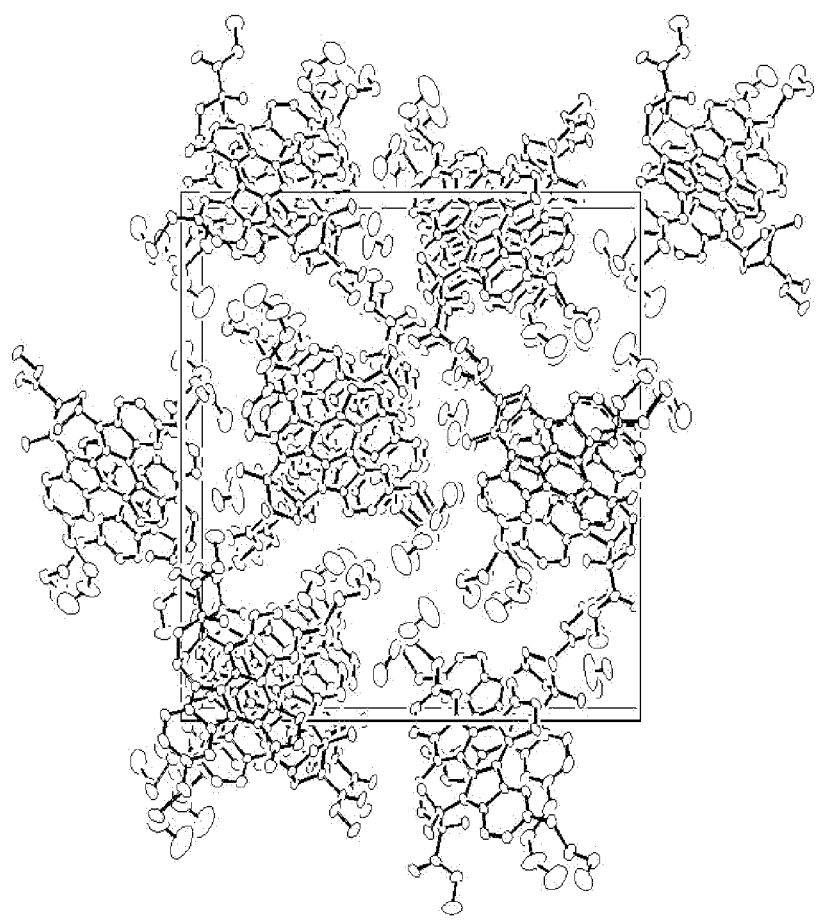
FIG. 19: Shows the packing of the molecules in Compound I alpha form.

The asymmetric unit of the crystal contains two Compound I units, and 0-1 solvent molecule. The solvent molecule may be either MeOH or water. In the structure determination the atoms corresponding to solvent were found with an occupancy of C2":0.70, O1":0.50 and O3":0.36. As the asymmetric unit contains 2 molecules of Compound I and one solvent site, full occupancy of the site would lead to a hemi-solvate. The atom numbering and the conformation of the two molecules in the asymmetric unit are shown in FIGS. 17-18, and the packing of the molecules in the crystal is shown in FIG. 19. The atom coordinates are given in Tables 2-4 below.

TABLE 2

Atom coordinates and equivalent isotropic displacement parameters for non-hydrogen atoms in molecule 1

| Label | X | y | z | U$_{eq}$ |
|---|---|---|---|---|
| C11 | −0.1062(9) | 0.2071(4) | 0.3154(5) | 0.119(4) |
| C12 | −0.0922(7) | 0.2369(3) | 0.2679(4) | 0.097(3) |
| C13 | 0.0402(5) | 0.3338(2) | 0.3022(2) | 0.0517(13) |
| C14 | 0.1485(4) | 0.37791(19) | 0.29800(19) | 0.0414(10) |
| C15 | 0.1730(5) | 0.4125(2) | 0.34227(19) | 0.0482(12) |
| C16 | 0.2157(4) | 0.38580(16) | 0.24912(17) | 0.0331(8) |
| C17 | 0.2642(4) | 0.4561(2) | 0.34044(17) | 0.0396(9) |
| C18 | 0.3097(3) | 0.42813(15) | 0.24665(15) | 0.0278(7) |
| C19 | 0.3347(4) | 0.46402(17) | 0.29167(15) | 0.0320(8) |
| C20 | 0.3600(3) | 0.37367(14) | 0.12235(15) | 0.0271(7) |
| C21 | 0.4226(3) | 0.42266(13) | 0.15070(14) | 0.0233(6) |
| C22 | 0.3963(3) | 0.44422(14) | 0.20324(14) | 0.0238(6) |
| C23 | 0.4700(3) | 0.48995(14) | 0.22250(14) | 0.0241(6) |
| C24 | 0.5184(3) | 0.41458(14) | 0.06419(15) | 0.0264(7) |
| C25 | 0.5168(3) | 0.44565(13) | 0.11709(13) | 0.0215(6) |
| C26 | 0.5911(3) | 0.49186(13) | 0.13513(13) | 0.0213(6) |
| C27 | 0.5642(3) | 0.51352(14) | 0.18804(13) | 0.0230(6) |
| C28 | 0.6972(3) | 0.52525(14) | 0.11306(14) | 0.0228(6) |
| C29 | 0.7277(3) | 0.56606(14) | 0.15290(13) | 0.0234(6) |
| C30 | 0.7685(4) | 0.52346(14) | 0.06360(14) | 0.0253(7) |
| C31 | 0.8269(4) | 0.60505(15) | 0.14453(16) | 0.0298(7) |
| C32 | 0.8676(3) | 0.56175(15) | 0.05494(15) | 0.0269(7) |
| C33 | 0.8947(4) | 0.60199(15) | 0.09522(16) | 0.0298(7) |
| C34 | 0.9449(4) | 0.55929(17) | 0.00224(16) | 0.0334(8) |
| C35 | 0.7493(5) | 0.6209(3) | −0.0511(2) | 0.0599(15) |
| C36 | 0.6968(6) | 0.5714(4) | −0.0827(3) | 0.083(2) |
| C37 | 0.5095(5) | 0.52590(19) | 0.37193(15) | 0.0392(9) |
| C38 | 0.4993(4) | 0.54457(16) | 0.31227(14) | 0.0293(7) |
| C39 | 0.4323(4) | 0.60294(16) | 0.30392(13) | 0.0297(7) |
| C40 | 0.4783(4) | 0.64389(17) | 0.34996(14) | 0.0345(9) |
| C41 | 0.6244(4) | 0.59217(15) | 0.24601(14) | 0.0279(7) |
| C42 | 0.4889(4) | 0.61943(15) | 0.24753(14) | 0.0282(7) |
| C43 | 0.6494(6) | 0.7018(2) | 0.3803(2) | 0.0550(13) |
| N10 | 0.6453(3) | 0.55884(12) | 0.19786(12) | 0.0273(6) |
| N8 | 0.4287(3) | 0.37320(12) | 0.07002(13) | 0.0299(6) |
| N9 | 0.4351(3) | 0.50175(13) | 0.27731(12) | 0.0276(6) |
| O3 | 0.5841(3) | 0.42305(12) | 0.02296(11) | 0.0336(6) |
| O4 | 0.6272(3) | 0.55359(11) | 0.29230(10) | 0.0294(5) |
| O5 | 0.2968(3) | 0.60128(12) | 0.30872(10) | 0.0334(6) |
| O6 | 0.4183(4) | 0.65298(14) | 0.39104(11) | 0.0475(8) |
| O7 | 0.5939(3) | 0.66596(12) | 0.33752(12) | 0.0417(7) |
| S1 | 0.05826(13) | 0.27639(6) | 0.25442(6) | 0.0573(3) |
| S2 | 0.92480(12) | 0.61925(5) | −0.04247(5) | 0.0462(3) |

TABLE 3

Atom coordinates and equivalent isotropic displacement parameters for non-hydrogen atoms in molecule2

| label | x | y | z | U$_{eq}$ |
|---|---|---|---|---|
| C11' | 0.3351(9) | 0.2274(4) | 0.3741(4) | 0.107(3) |
| C12' | 0.4501(6) | 0.2572(2) | 0.3960(2) | 0.0535(12) |
| C13' | 0.5141(4) | 0.32653(17) | 0.30754(16) | 0.0320(8) |
| C14' | 0.5962(3) | 0.33381(15) | 0.25640(15) | 0.0284(7) |
| C15' | 0.5818(4) | 0.29548(15) | 0.21266(15) | 0.0295(7) |
| C16' | 0.6877(3) | 0.37626(15) | 0.25214(15) | 0.0264(7) |
| C17' | 0.6562(4) | 0.29896(16) | 0.16476(15) | 0.0309(8) |

TABLE 3-continued

Atom coordinates and equivalent isotropic displacement parameters for non-hydrogen atoms in molecule2

| label | x | y | z | $U_{eq}$ |
|---|---|---|---|---|
| C18' | 0.7644(3) | 0.38027(14) | 0.20460(14) | 0.0245(7) |
| C19' | 0.7470(3) | 0.34216(14) | 0.16046(14) | 0.0246(7) |
| C20' | 0.9106(4) | 0.48618(16) | 0.27155(15) | 0.0295(7) |
| C21' | 0.9305(3) | 0.46300(14) | 0.21451(13) | 0.0242(6) |
| C22' | 0.8668(3) | 0.41839(14) | 0.18834(14) | 0.0241(7) |
| C23' | 0.9068(3) | 0.40231(14) | 0.13561(13) | 0.0228(6) |
| C24' | 1.0826(4) | 0.53365(16) | 0.22661(16) | 0.0315(8) |
| C25' | 1.0299(3) | 0.49163(14) | 0.18830(14) | 0.0250(7) |
| C26' | 1.0715(4) | 0.47630(14) | 0.13450(14) | 0.0254(7) |
| C27' | 1.0087(3) | 0.43081(14) | 0.10898(14) | 0.0244(6) |
| C28' | 1.1674(4) | 0.49705(15) | 0.09601(15) | 0.0268(7) |
| C29' | 1.1603(4) | 0.46218(15) | 0.04887(15) | 0.0285(7) |
| C30' | 1.2564(4) | 0.54209(16) | 0.09568(16) | 0.0306(7) |
| C31' | 1.2411(4) | 0.47048(16) | 0.00324(16) | 0.0345(8) |
| C32' | 1.3357(4) | 0.55112(17) | 0.05095(17) | 0.0339(8) |
| C33' | 1.3282(4) | 0.51493(18) | 0.00434(18) | 0.0374(9) |
| C34' | 1.4330(4) | 0.59844(19) | 0.0511(2) | 0.0440(10) |
| C35' | 1.2623(6) | 0.6661(3) | −0.0105(4) | 0.077(2) |
| C36' | 1.2183(8) | 0.7019(6) | 0.0358(4) | 0.136(5) |
| C37' | 0.7433(4) | 0.29800(15) | 0.04312(16) | 0.0338(8) |
| C38' | 0.8600(3) | 0.33047(15) | 0.06463(14) | 0.0262(7) |
| C39' | 0.9950(3) | 0.29655(14) | 0.06725(13) | 0.0230(6) |
| C40' | 0.9652(3) | 0.23557(15) | 0.05516(16) | 0.0300(7) |
| C41' | 1.0178(4) | 0.38189(15) | 0.01728(14) | 0.0296(7) |
| C42' | 1.0759(4) | 0.32366(14) | 0.02225(14) | 0.0267(7) |
| C43' | 0.9026(12) | 0.1491(3) | 0.0916(4) | 0.121(4) |
| N10' | 1.0640(3) | 0.42245(12) | 0.05746(12) | 0.0279(6) |
| N8' | 1.0092(3) | 0.53082(14) | 0.27242(14) | 0.0346(7) |
| N9' | 0.8335(3) | 0.35665(13) | 0.11793(12) | 0.0251(6) |
| O3' | 1.1773(3) | 0.56475(12) | 0.21928(12) | 0.0378(6) |
| O4' | 0.8822(3) | 0.37370(11) | 0.02552(10) | 0.0306(6) |
| O5' | 1.0630(3) | 0.30320(10) | 0.11731(10) | 0.0262(5) |
| O6' | 0.9505(3) | 0.21745(12) | 0.00864(13) | 0.0396(7) |
| O7' | 0.9482(4) | 0.20628(14) | 0.10012(14) | 0.0570(10) |
| S1' | 0.57873(14) | 0.26806(5) | 0.34631(5) | 0.0507(3) |
| S2' | 1.42524(15) | 0.64612(5) | −0.00597(6) | 0.0561(3) |

TABLE 4

Atom coordinates and equivalent isotropic displacement parameters and occupancy for atoms in the solvent entity

| label | x | y | z | $U_{eq}$ | Occupancy |
|---|---|---|---|---|---|
| O1" | 0.7366(10) | 0.4173(4) | −0.0687(3) | 0.080(4) | 0.499(16) |
| C2" | 0.6529(11) | 0.4259(10) | −0.1061(5) | 0.143(10) | 0.70(3) |
| O3" | 0.5557(18) | 0.4565(8) | −0.0933(5) | 0.097(8) | 0.36(2) |

Example 9

Melting Points

The melting points (cf. Example 7.4 above) obtained for the amorphous form and the crystalline alpha, beta, gamma delta and epsilon solid form of Compound I are shown in Table 1 below.

TABLE 1

| Form | Approx. melting temperature: |
|---|---|
| Amorphous | approx. 150° C. |
| α | 181-189° C. |
| β | approx. 211° C. |

TABLE 1-continued

| Form | Approx. melting temperature: |
|---|---|
| γ | 212-218° C. |
| δ | 211-223 |
| ε | approx. 182 |

The invention claimed is:

1. A crystalline form of Compound I, which has the formula:

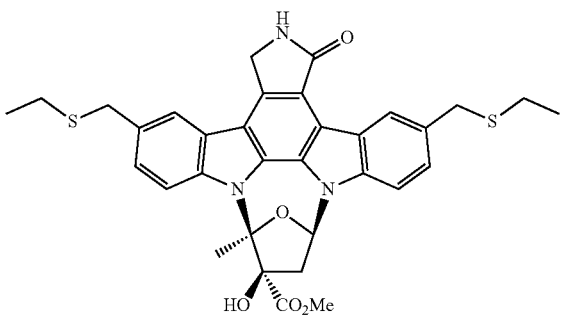 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

characterized by an X-Ray powder diffraction pattern comprising reflections at 9.6 degrees 2-theta, 11.5 degrees 2-theta, 12.5 degrees 2-theta, 16.7 degrees 2-theta, 19.3 degrees 2-theta, and 28.1 degrees 2-theta, when measured using CuKα radiation.

2. A crystalline form according to claim 1, wherein the X-ray powder diffraction pattern comprises reflections at 7.5 degrees 2-theta, 8.3 degrees 2-theta, 11.8 degrees 2-theta, 15.9 degrees 2-theta, 16.3 degrees 2-theta, 17.2 degrees 2-theta, 18.0 degrees 2-theta, and 21.0 degrees 2-theta, when measured using CuKα radiation.

3. A crystalline form of Compound I, which has the formula:

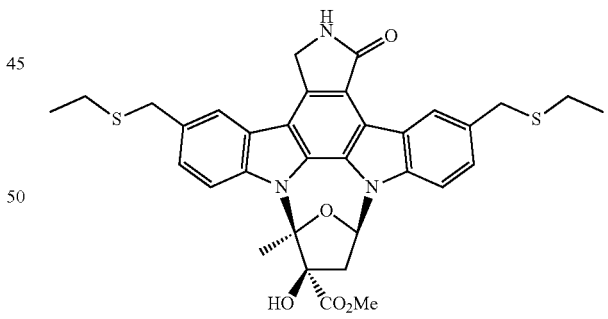

characterized by an X-Ray powder diffraction pattern comprising reflections at 5.2 degrees 2-theta, 10.1 degrees 2-theta, 10.4 degrees 2-theta, 13.2 degrees 2-theta, 15.1 degrees 2-theta, and 25.1 degrees 2-theta, when measured using CuKα radiation.

4. The crystalline form according to claim 3, wherein the X-ray powder diffraction pattern comprises reflections at 7.3 degrees 2-theta, 8.1 degrees 2-theta, 11.2 degrees 2-theta, 15.5 degrees 2-theta, 17.3 degrees 2-theta, 21.7 degrees 2-theta, and 23.8 degrees 2-theta, when measured using CuKα radiation.

5. A crystalline form of Compound I, which has the formula:

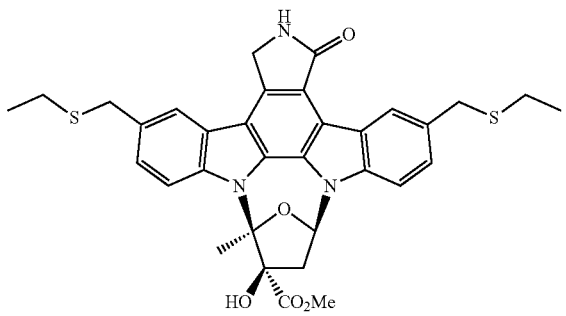 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

characterized by an X-Ray powder diffraction pattern comprising reflections at 9.7 degrees 2-theta, 12.1 degrees 2-theta, 16.1 degrees 2-theta, 18.3 degrees 2-theta, 22.1 degrees 2-theta, 22.2 degrees 2-theta, 25.7 degrees 2-theta, and 25.8 degrees 2-theta, when measured using CuKα radiation.

6. The crystalline form according to claim 5, wherein the X-Ray powder diffraction pattern comprises reflections at 7.3 degrees 2-theta, 8.3 degrees 2-theta, 11.1 degrees 2-theta, 11.7 degrees 2-theta, 15.6 degrees 2-theta, 17.3 degrees 2-theta, 20.9 degrees 2-theta, and 25.7 degrees 2-theta, when measured using CuKα radiation.

7. A crystalline form of Compound I, which has the formula:

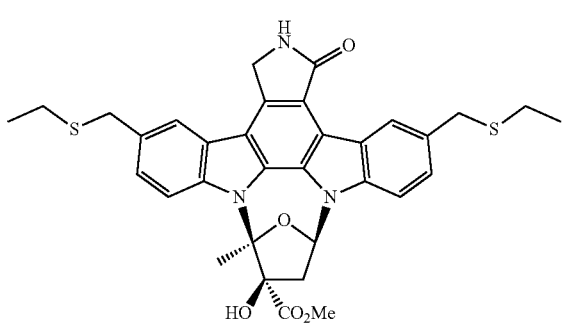 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

characterized by an X-Ray powder diffraction pattern comprising reflections at 6.6 degrees 2-theta, 8.9 degrees 2-theta, 10.7 degrees 2-theta, 11.7 degrees 2-theta, 24.4 degrees 2-theta, and 30.6 degrees 2-theta, when measured using CuKα radiation.

8. The crystalline form according to claim 7, wherein the X-Ray powder diffraction pattern comprises reflections at 13.7 degrees 2-theta, 17.0 degrees 2-theta, 18.5 degrees 2-theta, 18.8 degrees 2-theta, 19.2 degrees 2-theta, and 20.3 degrees 2-theta, when measured using CuKα radiation.

9. A crystalline form of Compound I, which has the formula:

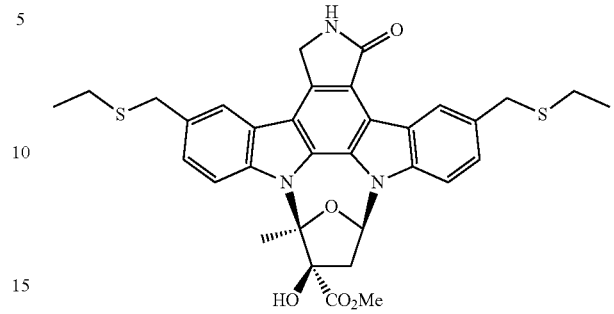

characterized by an X-Ray powder diffraction pattern comprising reflections at 8.9 degrees 2-theta, 9.2 degrees 2-theta, 10.2 degrees 2-theta, and 14.6 degrees 2-theta, when measured using CuKα radiation.

10. The crystalline form according to claim 9, wherein the X-Ray powder diffraction pattern comprises reflections at 12.6 degrees 2-theta, 14.2 degrees 2-theta, 17.0 degrees 2-theta, 18.6 degrees 2-theta, 20.4 degrees 2-theta, 21.1 degrees 2-theta, 23.9 degrees 2-theta, and 25.2 degrees 2-theta, when measured using CuKα radiation.

11. A solid pharmaceutical composition comprising a crystalline form of Compound I, which has the formula

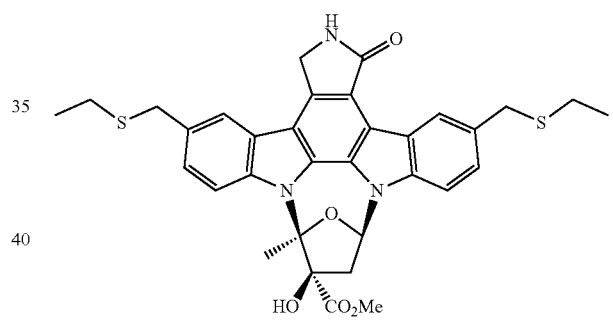

and a pharmaceutically acceptable excipient.

12. The pharmaceutical composition according to claim 11 wherein the composition is a solid solution formulation or a solid dispersion formulation.

13. The pharmaceutical composition according to claim 11 wherein the crystalline form of Compound I is characterized by an X-Ray powder diffraction pattern comprising reflections at 9.6 degrees 2-theta, 11.5 degrees 2-theta, 12.5 degrees 2-theta, 16.7 degrees 2-theta, 19.3 degrees 2-theta, and 28.1 degrees 2-theta, when measured using CuKα radiation.

14. The pharmaceutical composition according to claim 11 wherein the crystalline form of Compound I is characterized by an X-Ray powder diffraction pattern comprising reflections at 5.2 degrees 2-theta, 10.1 degrees 2-theta, 10.4 degrees 2-theta, 13.2 degrees 2-theta, 15.1 degrees 2-theta, and 25.1 degrees 2-theta, when measured using CuKα radiation.

15. The pharmaceutical composition according to claim 11 wherein the crystalline form of Compound I is characterized by an X-Ray powder diffraction pattern comprising reflections at 9.7 degrees 2-theta, 12.1 degrees 2-theta, 16.1 degrees 2-theta, 18.3 degrees 2-theta, 22.1 degrees 2-theta, 22.2 degrees 2-theta, 25.7 degrees 2-theta, and 25.8 degrees 2-theta, when measured using CuKα radiation.

16. The pharmaceutical composition according to claim 11 wherein the crystalline form of Compound I is characterized by an X-Ray powder diffraction pattern comprising reflections at 8.9 degrees 2-theta, 9.2 degrees 2-theta, 10.2 degrees 2-theta, and 14.6 degrees 2-theta, when measured using CuKα radiation.

17. The pharmaceutical composition according to claim 11 wherein the crystalline form of Compound I is characterized by an X-Ray powder diffraction pattern comprising reflections at 6.6 degrees 2-theta, 8.9 degrees 2-theta, 10.7 degrees 2-theta, 11.7 degrees 2-theta, 24.4 degrees 2-theta, and 30.6 degrees 2-theta, when measured using CuKα radiation.

18. A solid pharmaceutical composition comprising crystalline Compound I, which has the formula

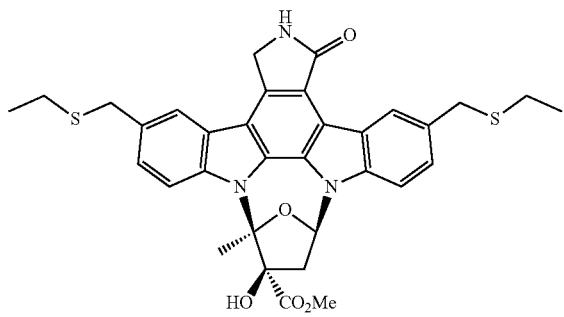 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

and a pharmaceutically acceptable excipient, wherein the crystalline Compound I is characterized by an X-ray powder diffraction pattern comprising reflections at 9.6 degrees 2-theta, 11.5 degrees 2-theta, 12.5 degrees 2-theta, 16.7 degrees 2-theta, 19.3 degrees 2-theta, and 28.1 degrees 2-theta; or by an X-ray powder diffraction pattern comprising reflections at 5.2 degrees 2-theta, 10.1 degrees 2-theta, 10.4 degrees 2-theta, 13.2 degrees 2-theta, 15.1 degrees 2-theta, and 25.1 degrees 2-theta; or by an X-ray powder diffraction pattern comprising reflections at 9.7 degrees 2-theta, 12.1 degrees 2-theta, 16.1 degrees 2-theta, 18.3 degrees 2-theta, 22.1 degrees 2-theta, 22.2 degrees 2-theta, 25.7 degrees 2-theta, and 25.8 degrees 2-theta; or by an X-ray powder diffraction pattern comprising reflections at 8.9 degrees 2-theta, 9.2 degrees 2-theta, 10.2 degrees 2-theta, and 14.6 degrees 2-theta; or by an X-ray powder diffraction pattern comprising reflections at 6.6 degrees 2-theta, 8.9 degrees 2-theta, 10.7 degrees 2-theta, 11.7 degrees 2-theta, 24.4 degrees 2-theta, and 30.6 degrees 2-theta.

* * * * *